United States Patent
Yu et al.

(10) Patent No.: US 11,559,531 B2
(45) Date of Patent: Jan. 24, 2023

(54) LIQUID FORMULATION COMPOSITIONS, MEDICAMENT DELIVERY DEVICES, AND METHODS OF PREPARATION AND USE THEREOF

(71) Applicants: SHENZHEN HIGHTIDE BIOPHARMACEUTICAL, LTD., Shenzhen (CN); SHANGHAI HIGHTIDE BIOPHARMACEUTICAL, LTD., Shanghai (CN)

(72) Inventors: Li Yu, Shenzhen (CN); James Gerry Ferguson, Shenzhen (CN)

(73) Assignee: Shenzhen HighTide Biopharmaceutical, Ltd., Shenzhen (CN)

(*) Notice: Subject to any disclaimer, the term of this patent is extended or adjusted under 35 U.S.C. 154(b) by 15 days.

(21) Appl. No.: 17/372,436

(22) Filed: Jul. 10, 2021

(65) Prior Publication Data
US 2022/0040203 A1    Feb. 10, 2022

Related U.S. Application Data

(60) Continuation of application No. 16/853,492, filed on Apr. 20, 2020, now abandoned, which is a division of application No. 15/303,451, filed as application No. PCT/CN2014/088010 on Sep. 30, 2014, now abandoned.

(51) Int. Cl.

| | | |
|---|---|---|
| *A61K 31/164* | (2006.01) | |
| *A61K 31/195* | (2006.01) | |
| *A61K 9/107* | (2006.01) | |
| *A61K 9/16* | (2006.01) | |
| *A61K 31/573* | (2006.01) | |
| *A61M 11/00* | (2006.01) | |
| *A61K 9/00* | (2006.01) | |
| *A61K 47/32* | (2006.01) | |
| *A61K 31/74* | (2006.01) | |
| *A61K 47/28* | (2006.01) | |
| *A61K 47/24* | (2006.01) | |
| *A61K 31/5383* | (2006.01) | |
| *A61K 47/10* | (2017.01) | |
| *A61P 27/04* | (2006.01) | |
| *A61P 27/02* | (2006.01) | |
| *A61P 11/00* | (2006.01) | |
| *A61P 11/02* | (2006.01) | |
| *A61P 11/12* | (2006.01) | |
| *A61P 27/16* | (2006.01) | |
| *A61J 1/05* | (2006.01) | |

(52) U.S. Cl.
CPC .......... *A61K 31/573* (2013.01); *A61K 9/0043* (2013.01); *A61K 9/0046* (2013.01); *A61K 9/0048* (2013.01); *A61K 9/107* (2013.01); *A61K 9/1617* (2013.01); *A61K 9/1641* (2013.01); *A61K 31/5383* (2013.01); *A61K 31/74* (2013.01); *A61K 47/10* (2013.01); *A61K 47/24* (2013.01); *A61K 47/28* (2013.01); *A61K 47/32* (2013.01); *A61M 11/00* (2013.01); *A61J 1/05* (2013.01); *A61M 2202/04* (2013.01); *A61M 2210/0612* (2013.01); *A61M 2210/0618* (2013.01); *A61M 2210/0662* (2013.01); *A61M 2210/0668* (2013.01)

(58) Field of Classification Search
None
See application file for complete search history.

(56) References Cited

U.S. PATENT DOCUMENTS 4,556,557 A * 12/1985 Reichert ................. A61K 31/14
                                                    514/642
4,863,725 A *  9/1989 Deckner .............. A61Q 19/007
                                                    514/847

(Continued)

FOREIGN PATENT DOCUMENTS

CN      1687260 A * 10/2005    ........... A61K 31/197
EP      1712220 A1 * 10/2006    ............. A61K 31/58

(Continued)

OTHER PUBLICATIONS

Collett, JH. "Poloxamer." Handbook of Pharmaceutical Excipients (2009) pp. 506-509. (Year: 2009).*

(Continued)

*Primary Examiner* — Bethany P Barham
*Assistant Examiner* — Peter Anthopolos
(74) *Attorney, Agent, or Firm* — Milstein Zhang & Wu LLC

(57) ABSTRACT

The invention provides liquid formulation compositions and medicament delivery devices, and methods for preparing and using the same. For example, the liquid formulation composition is an emulsion including a solvent and liquid particles, which includes surfactants and are dispersed in the solvent. The volume average particle size of the liquid particles is less than about 100 μm; the surface tension of the liquid formulation composition is less than about 60 mN/m; and the absolute value of zeta potential is greater than about 15 mV. The containment vessel may be a sprayer or a dropping device. The invention also provides methods for preparation of the liquid formulation compositions and medicament delivery devices as well as methods for using the same in treatment of various diseases and condition, for example, otitis media, otitis externa, rhinitis, sinusitis, lower respiratory tract inflammation, xerostomia (dry mouth), xerophthalmia (dry eyes) and xeromycteria (dry nose).

6 Claims, 1 Drawing Sheet

(56) References Cited

U.S. PATENT DOCUMENTS

| | | | | |
|---|---|---|---|---|
| 5,376,646 | A * | 12/1994 | Pittrof | A61K 8/678 |
| | | | | 514/629 |
| 5,801,199 | A * | 9/1998 | Greve | A61P 29/00 |
| | | | | 514/563 |
| 2005/0164979 | A1 * | 7/2005 | Gross | A61P 27/16 |
| | | | | 514/561 |
| 2006/0073173 | A1 * | 4/2006 | Banach | A61P 11/02 |
| | | | | 424/400 |
| 2007/0027048 | A1 * | 2/2007 | Schwind | C11D 3/32 |
| | | | | 510/112 |
| 2007/0104744 | A1 * | 5/2007 | Smith | C11D 3/362 |
| | | | | 510/112 |
| 2010/0173027 | A1 * | 7/2010 | Kroepke | A61K 8/342 |
| | | | | 514/738 |
| 2011/0230424 | A1 * | 9/2011 | Wagenaar | C11D 3/48 |
| | | | | 514/20.8 |
| 2013/0102679 | A1 * | 4/2013 | Holden | A61P 27/14 |
| | | | | 514/625 |
| 2013/0156868 | A1 * | 6/2013 | Schierstedt | A61K 9/0043 |
| | | | | 514/692 |

FOREIGN PATENT DOCUMENTS

| | | | | |
|---|---|---|---|---|
| WO | WO-9729738 | A1 * | 8/1997 | A61K 38/1709 |
| WO | WO-2008148573 | A2 * | 12/2008 | A61K 31/197 |

OTHER PUBLICATIONS

Haley, S. "Methylparaben." Handbook of Pharmaceutical Excipients (2009) pp. 441-445. (Year: 2009).*

* cited by examiner

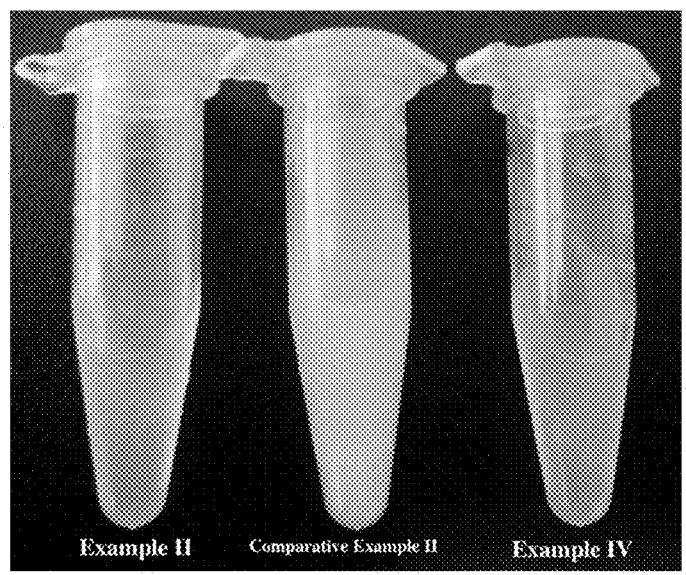

LIQUID FORMULATION COMPOSITIONS, MEDICAMENT DELIVERY DEVICES, AND METHODS OF PREPARATION AND USE THEREOF

PRIORITY CLAIMS AND RELATED APPLICATIONS

This application is a continuation of and claims the benefit of priority to U.S. Ser. No. 16/853,492, filed Apr. 20, 2021, which is the U.S. national phase of PCT/CN2014/088010, filed Sep. 30, 2014, which claims the benefit of priority from Chinese Application Nos. CN201410390825.9, CN201410391082.7, CN201410391083.1 and CN201410391084.6, all filed Aug. 8, 2014, the entire content of each of which is incorporated herein by reference in its entirety.

TECHNICAL FIELD OF THE INVENTION

The invention relates to liquid formulation compositions and medicament delivery devices, and methods for preparing and using the same.

BACKGROUND OF THE INVENTION

Otitis media, otitis externa, rhinitis and sinusitis are the most commonly occurred otorhinolaryngologic diseases.

Otitis media is an inflammatory lesion involving all or part of the structure of middle ear (including Eustachian tube, tympanic cavity, tympanic sinus and mastoid air cells) and are more common in children, but can occur at any age. There are two major types of otitis media, namely acute otitis media and otitis media with effusion. The former is usually symptomatic, especially ear pain, whereas the latter is most commonly without acute symptoms. Chronic suppurative otitis media, incorrectly called "chronic otitis media," is less common and is a complication of acute otitis media, and is associated with perforation of the ear drum, with or without drainage. All these conditions are most frequently associated with hearing loss. Barotitis media, or airplane ear, diver's ear, is caused by pressure change during aircraft takeoff and landing, water pressure increase during diving and the like. During a sudden increase in ambient pressure, gas must move from the nasopharynx into the middle ear to maintain equal pressure on both sides of the tympanic membrane. If the Eustachian tube is not functioning properly, the pressure in the middle ear is lower than the ambient pressure. The relative negative pressure in the middle ear results in retraction of the tympanic membrane and pain.

Otitis externa is an inflammation due to infection of external ear canal, and is often caused by injuries made during ear picking, ear scratching and/or contaminated water entering the external ear canal. Otitis externa can induce swelling of local skin of the external ear canal, accompanied by pain or tenderness, external ear itching and external ear secretion increase. There are two types of otitis externa, namely diffuse otitis externa and partial otitis externa. Because otitis externa commonly affects swimmers, it is sometimes known as swimmer's ear.

Rhinitis is the common name for symptoms caused by irritation or inflammation of nasal mucosa and includes allergic rhinitis, sinusitis, acute rhinitis and the like. The symptoms of rhinitis include nasal obstruction, runny nose, itching and sneezing, and severe rhinitis can cause headache, dizziness and decreased sense of smell. The causes and the symptoms of the above diseases are briefly described as follows:

Otitis media is generally caused by periodic open function disorders of the Eustachian tube. Eustachian tube (ET) is the only channel for air draining of the middle ear. The main function of Eustachian tube is to lead air in nasopharynx to the tympanic cavity to keep the pressure balanced on the two sides of tympanic membrane and further ensure normal vibration of the tympanic membrane. Mucosa of the Eustachian tube is connected with the mucosa of the tympanic cavity in nasopharynx, which is comprised with pseudostratified ciliated columnar epithelial cells and considerable number of secretory cells. Thin liquid (mucus) secreted by these cells can not only prevent the Eustachian tube from being opened completely, but also enable the Eustachian tube to be opened occasionally at appropriate opportunities, such as opening mouth, swallowing, yawning or chewing, thereby regulating the pressure in the tympanic cavity and keeping the balance of the pressures inside and outside the tympanic cavity. When the Eustachian tube has a dysfunction, the pressure imbalance on the two sides of the tympanum occurs while effusion in a cavity canal cannot be discharged timely, which can bring extreme agony to a patient. Earache is an early clinical symptom, and deafness, tinnitus, dizziness and other symptoms are easy to be ignored when being masked by earache. Systemic symptoms are different due to patient resistance and virulence of infecting bacteria and often comprise aversion to cold, fever, body discomfort, loss of appetite and the like. The characteristics of headache are represented as follows: the severe earache firstly occurs in the initial stage of the disease and then radiates to temporal occipitoparietal part on the same side as the affected ear, thereby causing unbearable hemi-headache. If the Eustachian tube is blocked, the pressure in the tympanic cavity may be reduced, and the external pressure is relatively increased, thereby enabling the tympanic membrane to sink inwards and affecting hearing.

Studies report that in samples of patients with secretory otitis media, the content of phospholipid representing a surfactant is discernibly reduced in comparison with that of a normal (healthy) control group. The difference has statistical significance ($p<0.01$), which confirms that the reduction of the surfactant in the patients with secretory otitis media is mainly shown in the nasopharynx, the middle ear and part of the Eustachian tube. The leads to an increase in the open pressure of the Eustachian tube and enables the compliance to be possible, causing the effusion in middle ear cavity and the retention of the effusion, resulting in secretory otitis media. (Qiu, et al, 1999 *Journal of West China University of Medical Sciences.* 30(3): 310-311.) The reduction of the content of the phospholipid is also reported in the patients with the rhinitis. (Sayed, et al. 2000 *J Laryngol Otol.* April; 114(4): 254-9; Schlosser, 2006 *Ann Otol Rhinol Laryngol Suppl.* September 196: 40-4.)

There are many reasons that give rise to otitis externa, most of which are bacterial infection-related and some are fungal infection-related or due to non-infectious skin diseases. When suffering from otitis externa, the patient usually has the following major symptoms: severe itching, swelling and pain of the external ear canal, as well as thick, white or yellow exudate. If the ear canal is blocked by the exudate, partial hearing loss will occur.

Under normal physiological conditions, mucus produced by the mucosa of nasal cavity can attract substances, such as dust, pollen and powder, as well as microbes, such as bacteria and viruses, and the like. The mucus can flow out from the front part of the nose or flow down from the rear part of the throat. When the nasal mucosa is subject to irritation or inflammation, excess mucus is produced which cannot be removed timely, so that nasal obstruction, runny nose, itching and/or sneezing are caused.

Normal paranasal sinuses are air cavities in craniofacial bones around the nasal cavity and comprise four pairs in total, namely maxillary sinuses, frontal sinuses, ethmoidal sinuses and sphenoidal sinuses. The mucosa is on the inner wall of each sinus and the sinuses respectively have certain parts, shapes and outlets. When suffering from sinusitis, the patient has mucosal congestion and swelling and a lot of mucopurulent or purulent nasal in the nasal cavity, resulting in severe nasal obstruction, purulent nasal, headache, dizziness and decreased sense of smell.

Lower respiratory tract inflammation mainly includes bronchitis, chronic bronchitis, pneumonia, bronchiectasis and the like. The main symptoms include cough, expectoration, asthma, chest pain, fever and the like. At present, antibiotics and antitussive and expectorant medicines are commonly used in clinical treatment.

Xeromycteria is a nasal disease that is mainly characterized by dryness in the nasal cavity. Rhinitis sicca in modern medicine is a chronic inflammatory disease of the nasal cavity, which is mainly represented as dryness of the nasal mucosa and reduction in nasal secretions. The symptoms include intranasal dryness, reduction in nasal secretions and prickling sensation or foreign body sensation in the nose, which often result in sneezing and burning sensations. The patient is often induced to pick the nose which can further cause a small amount of nasal bleeding, while the sense of smell is not generally impaired. The mucosa in the front bottom area of nasal septum is often erosive, small-piece thin scabs can be attached on the mucosa and bleeding often occurs after the small-piece thin scabs are removed. While the causes are not clear till now, it is generally believed that the disease is related to a indoor environment and external climate, and vitamin deficiency, anemia, heavy smoking and drinking can cause the change of the nasal mucosa and further cause the disease. As for the treatment of the disease, a lubricating liquid medicine can be partially dropped in the nose and the patient can be supplemented with vitamin A, vitamin B2, vitamin C, vitamin E and the like to enhance nutrition intake and balance.

Xerophthalmia is a general name of a variety of diseases, which cause abnormalities or dynamic abnormalities of quality or quantity of tears due to any reasons, reduce the stability of tear films and are accompanied by ocular discomfort and/or ocular surface tissue lesion characteristics. Xerophthalmia is also known as keratoconjunctivitis sicca. The common symptoms include dry eyes, fatigue, eye itching, foreign body sensations, burning heat sensations, thick secretions, fear of wind, photophobia and sensitivity to external stimuli. Sometimes, the eyes are too dry and lack basic tears, but the secretion of reflex tears is stimulated, thereby often causing tearing. In more severe cases, the eyes turn red, swollen, congested and keratinized, and corneal epithelium is broken and adhered with filaments. Such injuries can cause corneal and conjunctival lesions over time, which can further affect vision.

The tear film is mainly composed with phospholipid, protein, mucin, electrolyte and water. The ingredients of a lipid layer are mainly from meibomian gland, when in blinking (winking), lipids are compressed by eyelid, aggregated on a lower corneal water layer and dispersed like a horizontal belt. At the end of blinking (winking), the lipids are rapidly spread on the water liquid layer at a speed greater than the speed of eyelid open. The water layer is not directly exposed in air, and the evaporation of the tears is reduced. At present, literatures report that the most common reason causing dry eyes is meibomian gland dysfunction (MGD), which can affect the functions of the tear films and cause dry eyes. (Foulks, 2007 *Surv Ophthalmol*. July-August (4): 369-74; Xiao, et al. 2012 *Chinese Journal of Ophthalmology*. March, 48(3): 282-5.)

At present, treatment methods for xerophthalmia mainly are artificial tears, inflammation inhibition, promotion of tears secretion and the like. Treatment with artificial tears is the most common treatment approach, which is easiest to be accepted by patients. Commercially artificial tears are available, for example, Liposic (Bausch & Lomb), which contains the main ingredients of 1% medium chain triglyceride, 0.2% carbomer 980, sorbitol, sodium hydroxide and the like, as well as a preservative, namely 0.01% cetrimide; and Refresh Dry Eye Therapy (formerly known as Refresh Endura, Allergan), which contains the main ingredients of 1% polysorbate 80, 1% glycerol, carbomer, castor oil, mannitol, sodium hydroxide and the like.

Xerostomia is a symptom caused by saliva deficiency in mouth. The production and secretion of saliva are affected by various systemic, local, external and personal factors. As the secretion of saliva is reduced, the patient can feel xerostomia, foreign body sensations and burning sensations. When the patient chews food, especially relatively dry food, alimentary bolus cannot be formed, and swallowing is affected. Saliva secretion is insufficient, the washing effect to teeth and oral mucosa is also decreased, and the self-cleaning effect of the oral cavity becomes poor. As a result, a patient with xerostomia also has relatively high dental caries rate. Since xerostomia also affects the sense of taste, the appetite cannot be effectively stimulated, and the functions of a whole digestive system can also be affected.

At present, the treatment for xerostomia includes treatment against the causes of the disease and the symptoms. The treatment against the causes of the disease is most effective when the causes of the disease are clear. Taking medicine-induced dry mouth as an example, the dry mouth can be relieved by adjusting the medicines and the dosage thereof. As for dry mouth caused by increased consumption of saliva, reducing or eliminating mouth breathing can help. If dry mouth is caused by substantial destruction of salivary glands, such as radiotherapy of a malignant tumor at head and neck and Sjogren's syndrome, the dry mouth is currently mainly relieved by symptomatic treatment, and complications are further reduced.

Through the above description, it is clear that common characteristics of these diseases are that liquid secreted by the mucosa of the cavity canal is either increased and cannot be discharged timely due to infections or inflammation of the cavity canal (ears or nose), the cavity canal is blocked, and ear congestion, nasal congestion, pain, cough and other discomfortable symptoms are further caused. Or, dry eyes, dry mouth, dry nose, asthma and other discomfortable symptoms are caused by reduction of the secretions (nasal secretions, tear films and saliva) at the corresponding parts or decreased stability due to changes in the compositions of normal secretions.

At present, in clinical treatment, antibiotics, steroids and surgical treatment are commonly used. These treatment methods with the exception of surgery, however, cannot rapidly relieve ear congestion, nasal congestion, pain, cough, asthma, dry eyes, dry mouth, dry nose and other discomfortable symptoms of the patient in a short time (minutes-hours).

Therefore, an urgent unmet need exists for a product that can effectively relieve ear congestion, nasal congestion, pain, cough, asthma, dry eyes, dry mouth, dry nose and other discomfortable symptoms of the patients in a short time.

SUMMARY OF THE INVENTION

Technical problem to be solved by the invention includes providing compositions and medicament delivery devices, and methods for preparing and using the same, which can effectively treat ear congestion, nasal congestion, pain, cough, asthma, dry eyes, dry mouth, dry nose and other discomfortable diseases and conditions in a short time. The technical scheme adopted for solving the above technical problem is as follows.

In the past decades, people have attempted to utilize surfactants to solve the problems of otitis media, rhinitis and the like. There were, however, various problems emerged in developing effective products. For example, although a nasal wash product prepared by utilizing synthetic surfactants as ingredients could help the patient clear away mucus in nasal cavity and reduce nasal congestion symptom effectively, the ingredients in the product caused some patients to lose their sense of smell, which resulted a voluntary recall of the product from the market (NeilMed's SinuSurf Additive Causes Loss of Sense of Smell, http://www.texassinuscenter.com, accessed on Jul. 30, 2014).

Jang, et al. reported the effects of the nebulized pulmonary surfactant in a guinea pig otitis media model (Jang, et al. 2010 *Int J Pediatr Otorhinolaryngol*. January 74(1):71-4). The pulmonary surfactant used in the study was expensive, and a nebulizer is complex and inconvenient to use in many settings. Chandrasekha, et al. reported that the aerosolized surfactant was used in animal experiments for treatment of otitis media (Chandrasekha, et al., 2004 *Laryngoscope*. March 114(3):472-85). The formulation adopted there needed to employ a propellant, and the active ingredient existed in a solid form. Thus, in order to achieve the curative effect, the formulation must be moistened first and adhered to a target part to increase the onset time. Meanwhile, the propellant may cause irritation to the nasal cavity with local inflammation.

The invention provides a formulation, including a containment vessel and a liquid formulation composition contained in the containment vessel, wherein the liquid formulation composition is an emulsion including a solvent and liquid particles which contain surfactants and are dispersed in the solvent. The volume average particle size of the liquid particles is less than about 100 μm; the surface tension of the liquid formulation composition is less than about 60 mN/m and the absolute value of zeta potential of the liquid formulation composition is greater than about 15 mV; and the containment vessel is a sprayer or a dropping device.

When the liquid formulation composition disclosed herein is applied to the nasal cavity, the surfactant spreads on the nasal mucosa and gets in contact with the Eustachian tube opening in the back of nose. The surfactant further contacts with the surface of middle ear effusion. As the surface tension of the liquid formulation composition is relatively low (less than 60 mN/m), the surface tension of exudate at the mucosa of the Eustachian tube can be rapidly reduced, and the Eustachian tube can be opened more easily. Meanwhile, the liquid formulation composition is adhered on the mucosa of a cavity canal, and the lubricating effect is produced. As a result, the middle ear effusion can flow out smoothly. By eliminating the effusion and opening up the Eustachian tube, the ear pressure can be equalized, eliminating or alleviating the symptoms of tinnitus and headache. Meanwhile, the risk of infection is reduced, the elimination of inflammation is accelerated, and the healing time is shortened.

For the pus in external ear canal, on the one hand, the liquid formulation composition can reduce the surface tension of the pus. On the other hand, the liquid formulation composition adheres to the mucosa of the external ear canal so as to produce the lubricating effect, promoting the smooth outflow of the pus thereby reduce the symptoms of ear congestion and ear swelling. Based on the same mechanism of action, the liquid formulation composition can adhere to the surface of the mucosa of the nasal cavity, further promoting the clearing of the mucus in the nasal cavity and reducing the symptom of nasal congestion.

As known to the skilled artisan, one end of the Eustachian tube enters tympanic cavity from the front wall, the other end of the Eustachian tube enters nasopharynx, and the position is very hidden and is not conductive to treatment. The liquid formulation composition disclosed herein can be applied in a form of spray through a sprayer to effectively deliver the formulation to the Eustachian tube, the nasal cavity, paranasal sinuses and other target parts to realize the curative effect, or be applied to the external ear canal and the nasal cavity in the form of ear drops and nasal drops.

The treatment for lower respiratory tract inflammation of the invention is mainly as follows: the surfactant can reach trachea through the sprayer, moisten the trachea, reduce the irritation of the disease to the mucosa of the trachea, dilute sputum, easily cough out the sputum, reduce the surface tension of lung and relieve asthma. The formulation adopting the natural surfactant lecithin can moisten the trachea, reduce the surface tension of the lung, and repair the damaged mucosa.

The treatment for xeromycteria (or rhinitis sicca) of the invention is mainly as follows: the surfactant can effectively reach the nasal cavity through the sprayer or in the form of nasal drops, reduce the surface tension of the nasal cavity and the mucus and make up for a lack of liquid. The formulation prepared by adopting the natural surfactant lecithin can not only moisten the nasal cavity, but also repair the damaged mucosa.

The treatment for xerophthalmia of the invention is mainly as follows: by utilizing the property of nature surfactant for reducing the surface tension of the surfactant, the thickness of a tear lipid layer is increased to keep the stability of tear films, which can prolong the break-up time of the tear films, reduce the evaporation of tears and keep the quantity of ocular surface tears. The formulation prepared by adopting the natural surfactant lecithin can make up for the lack of lecithin in the tear lipid layer.

Research results show that the surface tension of the saliva in the oral cavity of the patient with xerostomia is discernibly higher than that of normal people (Cassie, et al. 2008 *Sleep*, Vol. 31, No. 3. "Upper Airway Surface Tension but not Upper Airway Collapsibility is Elevated in Primary Sjögren's Syndrome"). The surfactant in the invention can reduce the surface tension of the saliva of the patient with xerostomia, while simultaneously supplement saliva and relieve the symptom of dry mouth.

Compared to the aerosol and nebulization therapy, spraying does not need to utilize the propellant or the complex nebulizer. It uses a nasal spray device with the help of power produced by compressed air and spray out the mist particles to make a water type spray. Spraying has the advantages that the mist particles, which are sprayed out are thinner, are uniformly dispersed in the nasal cavity, less prone to loss, high in adhesion speed and allows rapid onset of action. Furthermore, the sprayer is less costly and has less stringent conditions for effective use. When spraying is the adopted form or treatment, the stability of the formulation is critical. In particular, sedimentation and the like in the formulation is undesirable and must be prevented or minimized.

Through extensive research and development, it is found that the liquid formulation composition disclosed herein is a stable emulsion or solution, which includes a liquid solvent and liquid particles dispersed in the solvent, wherein the liquid particles include a surfactant with desirable surface activity. Furthermore, the absolute value of zeta potential of the liquid formulation composition is greater than about 15 mV, and the volume average particle size of the liquid particles is less than about 100 μm. The liquid particles with the above characteristics can be stably dispersed in the solvent. The sedimentation phenomenon of the solid powder surfactant, which is easy to occur, can be avoided.

The liquid formulation composition is a colloidal dispersion system formed by the surfactant in the solvent. The zeta potential is an important indicator characterizing the stability of the dispersion system. On the premise that the volume average particle size of the liquid particles of the liquid formulation composition is less than about 100 μm, the absolute value of zeta potential of the liquid formulation composition is more than about 15 mV. The dispersion system with the above characteristics can remain relatively stable and is less prone to coagulation or agglomeration.

Meanwhile, when the liquid formulation composition is used in the spray form, the liquid particles having the surfactant and the solvent are sprayed together out of a sprayer in the form of mist droplets. When the liquid formulation composition is used in the form of nasal drops, the liquid formulation composition directly enters the nasal cavity. For example, after the liquid formulation composition reaches the Eustachian tube, the nasal cavity, the paranasal sinuses and other target parts, the liquid surfactant is directly dispersed on the mucosa of Eustachian tube and becomes in contact with middle ear effusion and nasal mucus. This causes a reduction in the surface tension of the middle ear effusion and the nasal mucus. The liquid surfactant is simultaneously adhered to the surface of the mucosa giving rise to a lubricating effect. Together, these help smoothly clear away the middle ear effusion and the nasal mucus, resulting in rapid relief of the discomfortable symptoms of the patient.

In addition, the liquid formulation composition disclosed herein has good stability, the main ingredients are from FDA's Generally Recognized Safe (GRAS) list, and the surfactant exists in the solvent in a liquid form. When the liquid formulation composition is used in the spray form, the requirements on spray pressure and other using conditions are low, and the liquid formulation composition only needs to adopt the conventional sprayer and does not need to adopt the propellant or the special nebulizer. Furthermore, the dissolution process which is necessary for the solid surfactant is not required for the liquid formulation at target sites, so the effectiveness can be achieved quickly; in addition, the liquid formulation composition does not need other substances to accelerate the dissolution at the target part.

Furthermore, in the liquid formulation composition disclosed herein, one of medicines for treating rhinitis, sinusitis, lower respiratory tract inflammation, otitis media, otitis externa, xerostomia, xerophthalmia and xeromycteria, or a combination thereof can be simultaneously added to perform targeted treatment against rhinitis, sinusitis, otitis media, otitis externa, lower respiratory tract inflammation, xerostomia, xerophthalmia and xeromycteria.

Therefore, in one aspect, the invention generally relates to a liquid formulation composition. The liquid formulation composition includes a solvent and a surfactant dissolved in the solvent. The liquid formulation composition is characterized by a surface tension of less than about 60 mN/m, and a pH value from about 5.0 to about 7.4.

In another aspect, the invention generally relates to a liquid formulation composition. The liquid formulation composition includes a solvent and liquid particles dispersed in the solvent, wherein the liquid particles include a surfactant. The liquid formulation composition is an emulsion. The volume average particle size of the liquid particles is less than about 100 μm. The liquid formulation composition is characterized by a surface tension of less than about 60 mN/m and an absolute value of zeta potential of greater than about 15 mV.

In yet another aspect, the invention generally relates to a liquid formulation composition. The liquid formulation composition includes: an active pharmaceutical ingredient; a solvent; and liquid formulation, the liquid formulation comprising a surfactant. The active pharmaceutical ingredient is selected from one of medicines for treating rhinitis, sinusitis, lower respiratory tract inflammation, otitis media, otitis externa, xerostomia, xerophthalmia, xeromycteria, or a combination thereof. The liquid formulation composition is characterized by a surface tension of less than about 60 mN/m, and a pH value from about 5.0 to about 7.4.

In yet another aspect, the invention generally relates to a liquid formulation composition. The liquid formulation composition includes: an active pharmaceutical ingredient; a solvent; and liquid particles dispersed in the solvent, the liquid particles including a surfactant. The liquid formulation composition is an emulsion. The volume average particle size of the liquid particles is less than about 100 μm. The active pharmaceutical ingredient is selected from one of medicines for treating rhinitis, sinusitis, lower respiratory tract inflammation, otitis media, otitis externa, xerostomia, xerophthalmia, xeromycteria, or a combination thereof. The liquid formulation composition is characterized by a surface tension of less than about 60 mN/m and an absolute value of zeta potential of greater than about 15 mV.

In yet another aspect, the invention generally relates to a medicament delivery device. The medicament delivery device includes: a containment vessel for holding a liquid including an outlet and a liquid formulation composition held in the containment vessel. The liquid formulation composition is a solution and includes a solvent and a surfactant. The liquid formulation composition is characterized by a surface tension of less than about 60 mN/m, and a pH value from about 5.0 to about 7.4.

In yet another aspect, the invention generally relates to a medicament delivery device. The medicament delivery device includes: a containment vessel for holding a liquid including an outlet and a liquid formulation composition held in the containment vessel. The liquid formulation composition is an emulsion and includes a solvent and, dispersed therein, liquid particles including a surfactant. The volume average particle size of the liquid particles is less than about 100 μm. The liquid formulation composition is characterized by a surface tension of less than about 60 mN/m and an absolute value of zeta potential of greater than about 15 mV.

In yet another aspect, the invention generally relates to a method for preparing a liquid formulation composition. The method includes: (S1) dissolving or dispersing a surfactant in a solvent to form a solution or a stable suspension; and (S2) adjusting the solution to form a liquid formulation composition characterized by a surface tension of less than about 60 mN/m and a pH value from about 5.0 to about 7.4.

In yet another aspect, the invention generally relates to a method for preparing a liquid formulation composition. The method includes: (S1) dissolving or dispersing a surfactant in a solvent with ultrasound of about 40 KHz to about 60 KHz for about 1 minute to about 3 minutes; and (S2) uniformly mixing an active pharmaceutical ingredient, the surfactant and a solvent under a stirring condition characterized by a rotational speed of more than 3000 rpm to form a liquid formulation composition characterized by a surface tension of less than about 60 mN/m and an absolute value of zeta potential of greater than about 15 mV.

In yet another aspect, the invention generally relates to a method for preparing the liquid formulation composition. The method includes: (S1) dissolving or dispersing a surfactant in a solvent with ultrasound of about 40 KHz to about 60 KHz for about 1 minute to about 3 minutes; and (S2) uniformly mixing an active pharmaceutical ingredient, the surfactant and a solvent under a stirring condition characterized by a rotational speed of more than 3000 rpm to form a liquid formulation composition in the form of an emulsion. The liquid formulation composition includes a solvent and, dispersed therein, liquid particles including a surfactant. The volume average particle size of the liquid particles is less than about 100 The liquid formulation composition is characterized by a surface tension of less than about 60 mN/m and an absolute value of zeta potential of more than about 15 mV. The active pharmaceutical ingredient is selected from one of medicines for treating rhinitis, sinusitis, lower respiratory tract inflammation, otitis media, otitis externa, xerostomia, xerophthalmia, xeromycteria, or a combination thereof.

In yet another aspect, the invention generally relates to a method for preparing the medicament delivery device. The method include: (S1) dissolving or dispersing a surfactant in a solvent with ultrasound of about 40 KHz to about 60 KHz for about 1 minute to about 3 minutes; and (S2) uniformly mixing the surfactant with a solvent under a stirring condition characterized by a rotational speed of more than 3000 rpm to form a liquid formulation. The liquid formulation composition is an emulsion and includes a solvent and, dispersed therein, liquid particles including a surfactant. The volume average particle size of the liquid particles is less than about 100 μm. The liquid formulation composition is characterized by a surface tension of less than about 60 mN/m and an absolute value of zeta potential of more than about 15 mV; and (S3) filling the liquid formulation composition into a containment vessel.

In yet another aspect, the invention generally relates to a method for treating, reducing, or preventing otitis media. The method includes administering to a subject in need thereof a liquid formulation composition disclosed herein, in an amount effective to treat, prevent, or reduce one or more diseases or disorders selected from rhinitis, sinusitis, lower respiratory tract inflammation, otitis media, otitis externa, xerostomia, xerophthalmia and xeromycteria.

In yet another aspect, the invention generally relates to a method for treating, reducing, or preventing otitis media. The method includes administering to a subject in need thereof a liquid formulation composition, using the medicament delivery device disclosed herein, in an amount effective to treat, prevent, or reduce one or more diseases or disorders selected from rhinitis, sinusitis, lower respiratory tract inflammation, otitis media, otitis externa, xerostomia, xerophthalmia and xeromycteria.

In yet another aspect, the invention generally relates to a method for treatment of otitis media using the liquid formulation composition of the invention.

In yet another aspect, the invention generally relates to a method for treatment of otitis externa using the liquid formulation composition of the invention.

In yet another aspect, the invention generally relates to a method for treatment of rhinitis using the liquid formulation composition of the invention.

In yet another aspect, the invention generally relates to a method for treatment of sinusitis using the liquid formulation composition of the invention.

In yet another aspect, the invention generally relates to a method for treatment of xerostomia using the liquid formulation composition of the invention.

In yet another aspect, the invention generally relates to a method for treatment of xerophthalmia using the liquid formulation composition of the invention.

In yet another aspect, the invention generally relates to a method for treatment of xeromycteria using the liquid formulation composition of the invention.

In yet another aspect, the invention generally relates to a method for treatment of lower respiratory tract inflammation using the liquid formulation composition of the invention.

In yet another aspect, the invention generally relates to a method for treatment of otitis media using the medicament delivery device of the invention.

In yet another aspect, the invention generally relates to a method for treatment of otitis externa using the medicament delivery device of the invention.

In yet another aspect, the invention generally relates to a method for treatment of rhinitis using the medicament delivery device of the invention.

In yet another aspect, the invention generally relates to a method for treatment of sinusitis using the medicament delivery device of the invention.

In yet another aspect, the invention generally relates to a method for treatment of xerostomia using the medicament delivery device of the invention.

In yet another aspect, the invention generally relates to a method for treatment of xerophthalmia using the medicament delivery device of the invention.

In yet another aspect, the invention generally relates to a method for treatment of xeromycteria using the medicament delivery device of the invention.

In yet another aspect, the invention generally relates to a method for treatment of lower respiratory tract inflammation using the medicament delivery device of the invention.

Thus, as disclosed herein, the liquid formulation compositions can be used through the nasal cavity for adjuvant treatment of rhinitis, sinusitis, lower respiratory tract inflammation, otitis media and xeromycteria; the liquid formulation compositions can be used through the oral cavity for adjuvant treatment of dry mouth caused by various reasons and lower respiratory tract inflammation; and the liquid formulation compositions can be used through eyes for adjuvant treatment of dry eyes.

BRIEF DESCRIPTION OF THE FIGURES

FIG. 1 is a sedimentation stability comparison of Example II, Example IV and Comparative example II in the test of sedimentation stability of the invention.

DEFINITIONS

Unless defined otherwise, all technical and scientific terms used herein have the same meaning as commonly understood by one of ordinary skill in the art to which this invention belongs.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the term "treating, reducing, or preventing a metabolic disorder" refers to ameliorating such a condition before or after it has occurred. As compared with an equivalent untreated control, such reduction or degree of prevention is at least 5%, 10%, 20%, 40%, 50%, 60%, 80%, 90%, 95%, or 100% as measured by any standard technique.

As used herein, the term "pharmaceutically acceptable excipient, carrier, or diluent" refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

DETAILED DESCRIPTION OF THE INVENTION

In order to make the technical problem solved by the invention, the technical scheme and the beneficial effects to be more clearly understood, the invention is further described in detail with combination of figures and embodiments. It should be understood that the specific embodiments described herein are only used for explaining the invention rather than limiting the invention.

In one aspect, the invention generally relates to a liquid formulation composition. The liquid formulation composition includes a solvent and a surfactant dispersed or dissolved in the solvent to form a solution or a stable suspension. The liquid formulation composition is characterized by a surface tension of less than about 60 mN/m, and a pH value from about 5.0 to about 7.4.

In certain embodiments of the liquid formulation composition, the solvent includes one of water, ethanol, glycerol, medical silicone oil and edible vegetable oil, or a combination thereof. In certain preferred embodiments, the solvent includes water.

In certain embodiments, the surface tension of the liquid formulation composition is less than about 40 mN/m (e.g., less than about 35 mN/m, less than about 30 mN/m, less than about 27 mN/m, less than about 25 mN/m).

In certain embodiments, the pH value of the liquid formulation composition is from about 6.0 to about 7.4 (e.g., about 6.0, 6.2, 6.4, 6.6, 6.8, 7.0, 7.2, 7.4).

The surfactant(s) utilized in a liquid formulation composition of the invention may be any suitable surfactant, for example, a natural surfactant or a synthetic surfactant, or a combination thereof.

Exemplary surfactants include natural phospholipid, sterol, pulmonary surfactant, stearic acid, oleic acid, lauric acid, benzalkonium chloride, benzalkonium bromide, cetrimide, sorbitan fatty acid, polysorbate, polyoxyethylene stearate, polyoxyethylene-fatty alcohol ether, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof.

In certain embodiments, the surfactant includes one of lecithin, sterol, pulmonary surfactant, poloxamer, dipalmitoyl phosphatidylcholine, cholesterol, cholesteryl ester, phosphatidyl ethanolamine, phosphatidylglycerol, phosphatidylserine, polyethylene glycol, phosphatidylserine, or a combination thereof.

In certain embodiments of the liquid formulation composition, the content of the surfactant is in the range from about 0.0001 wt % to about 25.0 wt %, and the content of the solvent is in the range from about 75.0 wt % to about 99.9999 wt %.

In certain embodiments, the liquid formulation composition includes an active pharmaceutical ingredient, wherein the active pharmaceutical ingredient is selected from one of medicines for treating rhinitis, sinusitis, lower respiratory tract inflammation, otitis media, otitis externa, xerostomia, xerophthalmia, xeromycteria, or a combination thereof.

Any suitable active pharmaceutical ingredients may be utilized. For example active pharmaceutical ingredient of the liquid formulation composition may include one of cortisone, hydrocortisone, beclomethasone, triamcinolone acetonide, mometasone, dexamethasone, fluocinolone acetonide, budesonide, fluticasone, ephedrine hydrochloride, xylometazoline hydrochloride, levocabastine hydrochloride, azelastine hydrochloride, fructus xanthii, dandelion, radix scutellariae, bitter gourd, herba ephedrae, flos magnoliae, herba asari, radix angelicae dahuricae, rhizome acori tatarinowii, catechu, Longjing tea, cortex phellodendri, ofloxacin, levofloxacin, norfloxacin, lomefloxacin, tosufloxacin, sparfloxacin, roxithromycin, chloromycetin, penicillin, clindamycin, nitrofurazone, amoxicillin, ampicillin, clavulanate potassium, cefaclor, cefixime, cefdinir, cephradine, cephalexin, cefpodoxime, cefuroxime axetil, cefprozil, azithromycin, minocycline, acetyl midecamycin, acetylspiramycin, metronidazole, musk, potassium aluminium sulfate anhydrous, calamine, borneol, cochineal, cacumen platycladi, echinacea root, baptisia tinctoria root, D-panthenol, glycerin, hyaluronic acid, butanediol, polyethylene glycol, propanediol, hexanediol, xylitol, sorbitol, or a combination thereof.

In certain embodiments of the liquid formulation composition, the content of the surfactant is in the range from about 0.0001 wt % to about 25.0 wt %, the content of the solvent is in the range from about 70.0 wt % to about 99.9989 wt %, and the content of the active pharmaceutical ingredient is in the range from about 0.001 wt % to about 5.0 wt %.

The liquid formulation composition of the invention may further include one of bacteriostatic agent, flavoring agent, stabilizer, antioxidant, or a combination thereof.

In certain embodiments of the liquid formulation composition, the bacteriostatic agent includes one of parabens or its salts, benzoic acid or its salts, benzyl alcohol, phenylethanol, phenylacetic acid, phenoxyethanol, lauric acid monoglyceride, chlorobutanol, sorbic acid or its salts, calcium propionate, sodium propionate, dehydroacetic acid or its salts, sodium diacetate, benzalkonium chloride, benzalkonium bromide, cetrimide, chlorhexidine acetate, propanediol, carbon dioxide, nisin, natamycin, momordicin, thimerosal, mercuric nitrate, or a combination thereof.

In certain embodiments of the liquid formulation composition, the flavoring agent includes one of menthol, borneol, lemon oil, patchouli oil, cinnamon oil, jujube tincture, vanillin, peppermint oil, rose oil, eucalyptus oil, spearmint oil, eugenol, citral, jasmine extract, chrysanthemum extract, osmanthus extract, benzyl alcohol, phenylethanol, terpineol, methyl cyclopentenolone, α-amyl cinnamic aldehyde, butyric acid, hexanoic acid, isoamyl acetate, benzyl acetate, linalyl acetate, ethyl propionate, ethyl butyrate, isoamyl butyrate, benzyl butyrate, isoamyl isovalerate, ethyl hexanoate, ethyl heptanoate, ethyl lactate, allyl hexanoate, γ-nonalactone, ethyl maltol, allyl cyclohexyl propionate, maltol, γ-undecalactone, raspberry ketone, benzyl propionate, butyl butyrate, ethyl isovalerate, ethyl formate, benzyl benzoate, methyl pyrazine, 2,3-dimethyl pyrazine, trimethyl pyrazine, 2-acetyl pyrazine, 4-methyl-5-(β-hydroxyethyl) thiazole, 2-acetyl thiazole, 2,3,5,6-tetramethyl pyrazine, hexadecanal, ethyl vanillin, hydroxyl citronellal, or a combination thereof;

In certain embodiments of the liquid formulation composition, the stabilizer includes one of lecithin, poloxamer, saponin, tannin, glycerin fatty acid ester, sucrose fatty acid ester, propanediol fatty acid ester, cholesterol, cholesterol ester, polyethylene glycol, cellulose or its derivatives, dextrin, Arabic gum, tragacanth gum, pectin cellulose cheese, gelatin, alginic acid, or a combination thereof.

In certain embodiments of the liquid formulation composition, the antioxidant includes one of tert-butyl hydroxy anisole, butylated hydroxytoluene, tert-butyl hydroquinone, propyl gallate, ascorbyl palmitate, dilauryl thiodipropionate, 4-hexyl resorcinol, tocopherol, L-ascorbic acid, D-sodium erythorbate, tea polyphenols, rosemary extract, ginger extract, sugar alcohols, amino acids, or a combination thereof.

In certain embodiments of the liquid formulation composition, the content of the surfactant is in the range from about 0.0001 wt % to about 25.0 wt %, the content of the solvent is in the range from about 63.0 wt % to about 99.9879 wt %, the content of the bacteriostatic agent is in the range from about 0.001 wt % to about 2.0 wt %, the content of the flavoring agent is in the range from about 0.01 wt % to about 5.0 wt %, and the content of the antioxidant is in the range from about 0.001 wt % to 5.0 wt %. In certain embodiments of the liquid formulation composition, the content of the surfactant is in the range from about 0.0001 wt % to about 25.0 wt %, the content of the solvent is in the range from about 58.0 wt % to about 99.9869 wt %, the content of the bacteriostatic agent is in the range from about 0.001 wt % to about 2.0 wt %, the content of the flavoring agent is in the range from about 0.01 wt % to about 5.0 wt %, and the content of the antioxidant is in the range from about 0.001 wt % to 5.0 wt %, the content of the active pharmaceutical ingredient the content of which is in the range from about 0.001 wt % to about 5.0 wt %.

In another aspect, the invention generally relates to a liquid formulation composition. The liquid formulation composition includes a solvent and liquid particles dispersed in the solvent, wherein the liquid particles including a surfactant. The liquid formulation composition is an emulsion. The volume average particle size of the liquid particles is less than about 100 μm. The liquid formulation composition is characterized by a surface tension of less than about 60 mN/m and an absolute value of zeta potential of greater than about 15 mV.

In certain embodiments of the liquid formulation composition, the solvent includes one of water, ethanol, glycerol, medical silicone oil and edible vegetable oil, or a combination thereof. In certain preferred embodiments, the solvent includes water.

In certain embodiments, the absolute value of zeta potential of the liquid formulation composition is greater than about 20 mV (e.g., great than about 25 mV, great than about 30 mV, great than about 35 mV, great than about 40 mV, great than about 40 mV, great than about 45 mV, great than about 50 mV).

In certain embodiments of the liquid formulation composition, the volume average particle size of the liquid particles is from about 50 nm to about 100 μm (e.g., from about 100 nm to about 100 μm, from about 500 nm to about 100 μm, from about 1 μm to about 100 μm, from about 10 μm to about 100 μm, from about 50 nm to about 50 μm, from about 50 nm to about 10 μm, from about 50 nm to about 5 μm, from about 50 nm to about 1 μm).

In certain embodiments, the volume average particle size of the liquid particles is from about 1 μm to about 100 μm (e.g., from about 1 μm to about 10 μm, from about 5 μm to about 100 μm, from about 20 μm to about 100 μm, from about 50 μm to about 100 μm, from about 1 μm to about 50 μm, from about 1 μm to about 20 μm, from about 1 μm to about 10 μm). In certain embodiments, the volume average particle size of the liquid particles is from about 500 nm to about 1 μm. In certain embodiments, the volume average particle size of the liquid particles is from about 50 nm to about 500 nm (e.g., from about 100 nm to about 500 nm, from about 200 nm to about 500 nm, from about 50 nm to about 300 nm, from about 50 nm to about 200 nm, from about 50 nm to about 100 nm).

In certain embodiments, the pH value of the liquid formulation composition is from about 5.0 to about 7.4 (e.g., from about 5.5 to about 7.4, from about 6.0 to about 7.4, from about 7.0 to about 7.4, from about 5.0 to about 7.0, from about 5.0 to about 6.5, from about 5.0 to about 6.0, from about 5.0 to about 5.5).

In certain embodiments, the surface tension of the liquid formulation composition is less than about 40 mN/m (e.g., less than about 35 mN/m, less than about 30 mN/m, less than about 27 mN/m, less than about 25 mN/m).

The surfactant(s) utilized in a liquid formulation composition of the invention may be any suitable surfactant, for example, a natural surfactant or a synthetic surfactant, or a combination thereof.

Exemplary surfactants include natural phospholipid, sterol, pulmonary surfactant, stearic acid, oleic acid, lauric acid, benzalkonium chloride, benzalkonium bromide, cetrimide, sorbitan fatty acid, polysorbate, polyoxyethylene stearate, polyoxyethylene-fatty alcohol ether, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof.

In certain embodiments, the surfactant includes one of lecithin, sterol, pulmonary surfactant, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof.

In certain embodiments of the liquid formulation composition, the content of the surfactant is in the range from about 0.1 wt % to about 25.0 wt %, and the content of the solvent is in the range from about 75.0 wt % to about 99.9 wt %.

In certain embodiments, the liquid formulation composition further includes one of bacteriostatic agent, flavoring agent, stabilizer, antioxidant, or a combination thereof.

In certain embodiments, the bacteriostatic agent includes one of parabens or its salts, benzoic acid or its salts, benzyl alcohol, phenylethanol, phenylacetic acid, phenoxyethanol, lauric acid monoglyceride, chlorobutanol, sorbic acid or its salts, calcium propionate, sodium propionate, dehydroacetic acid or its salts, sodium diacetate, benzalkonium chloride, benzalkonium bromide, cetrimide, chlorhexidine acetate, propanediol, carbon dioxide, nisin, natamycin, momordicin, thimerosal, mercuric nitrate, or a combination thereof.

In certain embodiments, the flavoring agent includes one of menthol, borneol, lemon oil, patchouli oil, cinnamon oil, jujube tincture, vanillin, peppermint oil, rose oil, eucalyptus oil, spearmint oil, eugenol, citral, jasmine extract, chrysanthemum extract, osmanthus extract, benzyl alcohol, phenylethanol, terpineol, methyl cyclopentenolone, α-amyl cinnamic aldehyde, butyric acid, hexanoic acid, isoamyl acetate, benzyl acetate, linalyl acetate, ethyl propionate, ethyl butyrate, isoamyl butyrate, benzyl butyrate, isoamyl isovalerate, ethyl hexanoate, ethyl heptanoate, ethyl lactate, allyl hexanoate, γ-nonalactone, ethyl maltol, allyl cyclohexyl propionate, maltol, γ-undecalactone, raspberry ketone, benzyl propionate, butyl butyrate, ethyl isovalerate, ethyl formate, benzyl benzoate, methyl pyrazine, 2,3-dimethyl pyrazine, trimethyl pyrazine, 2-acetyl pyrazine, 4-methyl-5-(β-hydroxyethyl) thiazole, 2-acetyl thiazole, 2,3,5,6-tetramethyl pyrazine, hexadecanal, ethyl vanillin, hydroxyl citronellal, or a combination thereof;

In certain embodiments, the stabilizer includes one of lecithin, poloxamer, saponin, tannin, glycerin fatty acid ester, sucrose fatty acid ester, propanediol fatty acid ester, cholesterol, cholesterol ester, polyethylene glycol, cellulose or its derivatives, dextrin, Arabic gum, tragacanth gum, pectin cellulose cheese, gelatin, alginic acid, or a combination thereof.

In certain embodiments, the antioxidant includes one of tert-butyl hydroxy anisole, butylated hydroxytoluene, tert-butyl hydroquinone, propyl gallate, ascorbyl palmitate, dilauryl thiodipropionate, 4-hexyl resorcinol, tocopherol, L-ascorbic acid, D-sodium erythorbate, tea polyphenols, rosemary extract, ginger extract, sugar alcohols, amino acids, or a combination thereof.

In certain embodiments of the liquid formulation composition, the content of the surfactant is in the range from about 0.1 wt % to about 25.0 wt %, the content of the solvent is in the range from about 58.0 wt % to about 99.878 wt %, the content of the bacteriostatic agent is in the range from about 0.001 wt % to about 2.0 wt %, the content of the flavoring agent is in the range from about 0.01 wt % to about 5.0 wt %, the content of the stabilizer is in the range from about 0.01 wt % to about 5.0 wt %, and the content of the antioxidant is in the range from about 0.001 wt % to 5.0 wt %.

In yet another aspect, the invention generally relates to a liquid formulation composition. The liquid formulation composition includes: an active pharmaceutical ingredient; a solvent; and liquid particles dispersed in the solvent, the liquid particles including a surfactant. The liquid formulation composition is an emulsion. The volume average particle size of the liquid particles is less than about 100 μm. The active pharmaceutical ingredient is selected from one of medicines for treating rhinitis, sinusitis, lower respiratory tract inflammation, otitis media, otitis externa, xerostomia, xerophthalmia, xeromycteria, or a combination thereof. The liquid formulation composition is characterized by a surface tension of less than about 60 mN/m and an absolute value of zeta potential of greater than about 15 mV.

In certain embodiments of the liquid formulation composition, the solvent includes one of water, ethanol, glycerol, medical silicone oil and edible vegetable oil, or a combination thereof. In certain preferred embodiments, the solvent includes water.

In certain embodiments, the absolute value of zeta potential of the liquid formulation composition is greater than about 20 mV (e.g., great than about 25 mV, great than about 30 mV, great than about 35 mV, great than about 40 mV, great than about 40 mV, great than about 45 mV, great than about 50 mV).

In certain embodiments of the liquid formulation composition, the volume average particle size of the liquid particles is from about 50 nm to about 100 μm (e.g., from about 100 nm to about 100 μm, from about 500 nm to about 100 μm, from about 1 μm to about 100 μm, from about 10 μm to about 100 μm, from about 50 nm to about 50 μm, from about 50 nm to about 10 μm, from about 50 nm to about 5 μm, from about 50 nm to about 1 μm).

In certain embodiments, the volume average particle size of the liquid particles is from about 1 μm to about 100 μm (e.g., from about 1 μm to about 10 μm, from about 5 μm to about 100 μm, from about 20 μm to about 100 μm, from about 50 μm to about 100 μm, from about 1 μm to about 50 μm, from about 1 μm to about 20 μm, from about 1 μm to about 10 μm). In certain embodiments, the volume average particle size of the liquid particles is from about 500 nm to about 1 μm. In certain embodiments, the volume average particle size of the liquid particles is from about 50 nm to about 500 nm (e.g., from about 100 nm to about 500 nm, from about 200 nm to about 500 nm, from about 50 nm to about 300 nm, from about 50 nm to about 200 nm, from about 50 nm to about 100 nm).

In certain embodiments, the pH value of the liquid formulation composition is from about 5.0 to about 7.4 (e.g., from about 5.5 to about 7.4, from about 6.0 to about 7.4, from about 7.0 to about 7.4, from about 5.0 to about 7.0, from about 5.0 to about 6.5, from about 5.0 to about 6.0, from about 5.0 to about 5.5).

In certain embodiments, the surface tension of the liquid formulation composition is less than about 40 mN/m (e.g., less than about 35 mN/m, less than about 30 mN/m, less than about 27 mN/m, less than about 25 mN/m).

The surfactant(s) utilized in a liquid formulation composition of the invention may be any suitable surfactant, for example, a natural surfactant or a synthetic surfactant, or a combination thereof.

Exemplary surfactants include natural phospholipid, sterol, pulmonary surfactant, stearic acid, oleic acid, lauric acid, benzalkonium chloride, benzalkonium bromide, cetrimide, sorbitan fatty acid, polysorbate, polyoxyethylene stearate, polyoxyethylene-fatty alcohol ether, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof.

In certain embodiments, the surfactant includes one of lecithin, sterol, pulmonary surfactant, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof.

Any suitable active pharmaceutical ingredients may be utilized. For example active pharmaceutical ingredient of the liquid formulation composition may include one of cortisone, hydrocortisone, beclomethasone, triamcinolone acetonide, mometasone, dexamethasone, fluocinolone acetonide, budesonide, fluticasone, ephedrine hydrochloride, xylometazoline hydrochloride, levocabastine hydrochloride, azelastine hydrochloride, fructus xanthii, dandelion, radix scutellariae, bitter gourd, herba ephedrae, flos magnoliae, herba asari, radix angelicae dahuricae, rhizome acori tatarinowii, catechu, Longjing tea, cortex phellodendri, ofloxacin, levofloxacin, norfloxacin, lomefloxacin, tosufloxacin, sparfloxacin, roxithromycin, chloromycetin, penicillin, clindamycin, nitrofurazone, amoxicillin, ampicillin, clavulanate potassium, cefaclor, cefixime, cefdinir, cephradine, cephalexin, cefpodoxime, cefuroxime axetil, cefprozil, azithromycin, minocycline, acetyl midecamycin, acetylspiramycin, metronidazole, musk, potassium aluminium sulfate anhydrous, calamine, borneol, cochineal, cacumen platycladi, echinacea root, baptisia tinctoria root, D-panthenol, glycerin, hyaluronic acid, butanediol, polyethylene glycol, propanediol, hexanediol, xylitol, sorbitol, or a combination thereof.

In certain embodiments of the liquid formulation composition, the content of the surfactant is in the range from about 0.1 wt % to about 25.0 wt %; the content of the solvent is in the range from about 70.0 wt % to about 99.899 wt %; and the content of the active pharmaceutical ingredient is in the range from about 0.001 wt % to about 5.0 wt %.

In certain embodiments, the liquid formulation composition further includes one of bacteriostatic agent, flavoring agent, stabilizer, antioxidant, or a combination thereof.

In certain embodiments, the bacteriostatic agent includes one of parabens or its salts, benzoic acid or its salts, benzyl alcohol, phenylethanol, phenylacetic acid, phenoxyethanol, lauric acid monoglyceride, chlorobutanol, sorbic acid or its salts, calcium propionate, sodium propionate, dehydroacetic acid or its salts, sodium diacetate, benzalkonium chloride, benzalkonium bromide, cetrimide, chlorhexidine acetate, propanediol, carbon dioxide, nisin, natamycin, momordicin, thimerosal, mercuric nitrate, or a combination thereof.

In certain embodiments, the flavoring agent includes one of menthol, borneol, lemon oil, patchouli oil, cinnamon oil, jujube tincture, vanillin, peppermint oil, rose oil, eucalyptus oil, spearmint oil, eugenol, citral, jasmine extract, chrysanthemum extract, osmanthus extract, benzyl alcohol, phenylethanol, terpineol, methyl cyclopentenolone, α-amyl cinnamic aldehyde, butyric acid, hexanoic acid, isoamyl acetate, benzyl acetate, linalyl acetate, ethyl propionate, ethyl butyrate, isoamyl butyrate, benzyl butyrate, isoamyl isovalerate, ethyl hexanoate, ethyl heptanoate, ethyl lactate, allyl hexanoate, γ-nonalactone, ethyl maltol, allyl cyclohexyl propionate, maltol, γ-undecalactone, raspberry ketone, benzyl propionate, butyl butyrate, ethyl isovalerate, ethyl formate, benzyl benzoate, methyl pyrazine, 2,3-dimethyl pyrazine, trimethyl pyrazine, 2-acetyl pyrazine, 4-methyl-5-(β-hydroxyethyl) thiazole, 2-acetyl thiazole, 2,3,5,6-tetramethyl pyrazine, hexadecanal, ethyl vanillin, hydroxyl citronellal, or a combination thereof.

In certain embodiments, the stabilizer includes one of lecithin, poloxamer, saponin, tannin, glycerin fatty acid ester, sucrose fatty acid ester, propanediol fatty acid ester, cholesterol, cholesterol ester, polyethylene glycol, cellulose or its derivatives, dextrin, Arabic gum, tragacanth gum, pectin cellulose cheese, gelatin, alginic acid, or a combination thereof; and In certain embodiments, the antioxidant includes one of tert-butyl hydroxy anisole, butylated hydroxytoluene, tert-butyl hydroquinone, propyl gallate, ascorbyl palmitate, dilauryl thiodipropionate, 4-hexyl resorcinol, tocopherol, L-ascorbic acid, D-sodium erythorbate, tea polyphenols, rosemary extract, ginger extract, sugar alcohols, amino acids, or a combination thereof.

In certain embodiments of the liquid formulation composition, the content of the surfactant is in the range from about 0.1 wt % to about 25.0 wt %, the content of the solvent is in the range from about 53.0 wt % about 99.877 wt %, the content of the bacteriostatic agent is in the range from about 0.001 wt % to about 2.0 wt %, the content of the flavoring agent is in the range from about 0.01 wt % to about 5.0 wt %, the content of the stabilizer is in the range from about 0.01 wt % to about 5.0 wt %, the content of the antioxidant is in the range from about 0.001 wt % to about 5.0 wt %, and the content of the active pharmaceutical ingredient is in the range from about 0.001 wt % to about 5.0 wt %.

In yet another aspect, the invention generally relates to a medicament delivery device. The medicament delivery device includes: a containment vessel for holding a liquid including an outlet and a liquid formulation composition held in the containment vessel. The liquid formulation composition is an emulsion and includes a solvent and, dispersed therein, liquid particles including a surfactant. The volume average particle size of the liquid particles is less than about 100 μm. The liquid formulation composition is characterized by a surface tension of less than about 60 mN/m and an absolute value of zeta potential of greater than about 15 mV.

In certain embodiments of the medicament delivery device, the containment vessel is configured to function as a sprayer, allowing controlled spraying of the liquid formulation composition out of the outlet.

In certain embodiments of the medicament delivery device, the containment vessel is configured to function as a dropping device, allowing controlled dropping of the liquid formulation composition out of the outlet.

In certain embodiments of the medicament delivery device, the absolute value of zeta potential of the liquid formulation composition is greater than about 20 mV (e.g., great than about 25 mV, great than about 30 mV, great than about 35 mV, great than about 40 mV, great than about 40 mV, great than about 45 mV, great than about 50 mV).

In certain embodiments of the medicament delivery device, the volume average particle size of the liquid particles is from about 50 nm to about 100 μm (e.g., from about 100 nm to about 100 µm, from about 500 nm to about 100 µm, from about 1 µm to about 100 µm, from about 10 µm to about 100 µm, from about 50 nm to about 50 µm, from about 50 nm to about 10 µm, from about 50 nm to about 5 µm, from about 50 nm to about 1 µm).

In certain embodiments of the medicament delivery device, the volume average particle size of the liquid particles is from about 1 µm to about 100 µm (e.g., from about 1 µm to about 10 µm, from about 5 µm to about 100 µm, from about 20 µm to about 100 µm, from about 50 µm to about 100 µm, from about 1 µm to about 50 µm, from about 1 µm to about 20 µm, from about 1 µm to about 10 µm). In certain embodiments, the volume average particle size of the liquid particles is from about 500 nm to about 1 µm. In certain embodiments, the volume average particle size of the liquid particles is from about 50 nm to about 500 nm (e.g., from about 100 nm to about 500 nm, from about 200 nm to about 500 nm, from about 50 nm to about 300 nm, from about 50 nm to about 200 nm, from about 50 nm to about 100 nm).

In certain embodiments of the medicament delivery device, the pH value of the liquid formulation composition is from about 5.0 to about 7.4 (e.g., from about 5.5 to about 7.4, from about 6.0 to about 7.4, from about 7.0 to about 7.4, from about 5.0 to about 7.0, from about 5.0 to about 6.5, from about 5.0 to about 6.0, from about 5.0 to about 5.5).

In certain embodiments of the medicament delivery device, the surface tension of the liquid formulation composition is less than about 40 mN/m (e.g., less than about 35 mN/m, less than about 30 mN/m, less than about 27 mN/m, less than about 25 mN/m).

In certain embodiments of the medicament delivery device, the surfactant is a natural surfactant or a synthetic surfactant, or a combination thereof.

Exemplary surfactant includes one of natural phospholipid, sterol, pulmonary surfactant, stearic acid, oleic acid, lauric acid, benzalkonium chloride, benzalkonium bromide, cetrimide, sorbitan fatty acid, polysorbate, polyoxyethylene stearate, polyoxyethylene-fatty alcohol ether, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof.

In certain embodiments of the medicament delivery device, the surfactant includes one of lecithin, sterol, pulmonary surfactant, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof.

Any suitable solvent may be utilized. In certain embodiments of the medicament delivery device, the solvent is one of water, ethanol, glycerol, medical silicone oil and edible vegetable oil, or a combination thereof.

In certain embodiments of the medicament delivery device, in the liquid formulation composition, the content of the surfactant is in the range from about 0.1 wt % to about 25.0 wt %, and the content of the solvent is in the range from about 75.0 wt % to about 99.9 wt %.

In certain embodiments of the medicament delivery device, the liquid formulation composition further includes an active pharmaceutical ingredient, wherein the active pharmaceutical ingredient is selected from one of medicines for treating rhinitis, sinusitis, lower respiratory tract inflammation, otitis media, otitis externa, xerostomia, xerophthalmia, xeromycteria, or a combination thereof.

Any suitable active pharmaceutical ingredients may be utilized. For example, active pharmaceutical ingredient of the liquid formulation composition may include one of cortisone, hydrocortisone, beclomethasone, triamcinolone acetonide, mometasone, dexamethasone, fluocinolone acetonide, budesonide, fluticasone, ephedrine hydrochloride, xylometazoline hydrochloride, levocabastine hydrochloride, azelastine hydrochloride, fructus xanthii, dandelion, radix scutellariae, bitter gourd, herba ephedrae, flos magnoliae, herba asari, radix angelicae dahuricae, rhizome acori tatarinowii, catechu, Longjing tea, cortex phellodendri, ofloxacin, levofloxacin, norfloxacin, lomefloxacin, tosufloxacin, sparfloxacin, roxithromycin, chloromycetin, penicillin, clindamycin, nitrofurazone, amoxicillin, ampicillin, clavulanate potassium, cefaclor, cefixime, cefdinir, cephradine, cephalexin, cefpodoxime, cefuroxime axetil, cefprozil, azithromycin, minocycline, acetyl midecamycin, acetylspiramycin, metronidazole, musk, potassium aluminium sulfate anhydrous, calamine, borneol, cochineal, cacumen platycladi, echinacea root, baptisia tinctoria root, D-panthenol, glycerin, hyaluronic acid, butanediol, polyethylene glycol, propanediol, hexanediol, xylitol, sorbitol, or a combination thereof.

In certain embodiments of the medicament delivery device, in the liquid formulation composition, the content of the surfactant is in the range from about 0.1 wt % to about 25.0 wt %, the content of the solvent is in the range from about 70.0 wt % to about 99.899 wt %, and the content of the active pharmaceutical ingredient is in the range from about 0.001 wt % to about 5.0 wt %.

In certain embodiments of the medicament delivery device, the liquid formulation composition further includes one of bacteriostatic agent, flavoring agent, stabilizer, antioxidant, or a combination thereof.

In certain embodiments of the medicament delivery device, the bacteriostatic agent includes one of parabens or its salts, benzoic acid or its salts, benzyl alcohol, phenylethanol, phenylacetic acid, phenoxyethanol, lauric acid monoglyceride, chlorobutanol, sorbic acid or its salts, calcium propionate, sodium propionate, dehydroacetic acid or its salts, sodium diacetate, benzalkonium chloride, benzalkonium bromide, cetrimide, chlorhexidine acetate, propanediol, carbon dioxide, nisin, natamycin, momordicin, thimerosal, mercuric nitrate, or a combination thereof.

In certain embodiments of the medicament delivery device, the flavoring agent includes one of menthol, borneol, lemon oil, patchouli oil, cinnamon oil, jujube tincture, vanillin, peppermint oil, rose oil, eucalyptus oil, spearmint oil, eugenol, citral, jasmine extract, chrysanthemum extract, osmanthus extract, benzyl alcohol, phenylethanol, terpineol, methyl cyclopentenolone, α-amyl cinnamic aldehyde, butyric acid, hexanoic acid, isoamyl acetate, benzyl acetate, linalyl acetate, ethyl propionate, ethyl butyrate, isoamyl butyrate, benzyl butyrate, isoamyl isovalerate, ethyl hexanoate, ethyl heptanoate, ethyl lactate, allyl hexanoate, γ-nonalactone, ethyl maltol, allyl cyclohexyl propionate, maltol, γ-undecalactone, raspberry ketone, benzyl propionate, butyl butyrate, ethyl isovalerate, ethyl formate, benzyl benzoate, methyl pyrazine, 2,3-dimethyl pyrazine, trimethyl pyrazine, 2-acetyl pyrazine, 4-methyl-5-(β-hydroxyethyl) thiazole, 2-acetyl thiazole, 2,3,5,6-tetramethyl pyrazine, hexadecanal, ethyl vanillin, hydroxyl citronellal, or a combination thereof.

In certain embodiments of the medicament delivery device, the stabilizer includes one of lecithin, poloxamer, saponin, tannin, glycerin fatty acid ester, sucrose fatty acid ester, propanediol fatty acid ester, cholesterol, cholesterol ester, polyethylene glycol, cellulose or its derivatives, dextrin, Arabic gum, tragacanth gum, pectin cellulose cheese, gelatin, alginic acid, or a combination thereof.

In certain embodiments of the medicament delivery device, the antioxidant includes one of tert-butyl hydroxy anisole, butylated hydroxytoluene, tert-butyl hydroquinone, propyl gallate, ascorbyl palmitate, dilauryl thiodipropionate, 4-hexyl resorcinol, tocopherol, L-ascorbic acid, D-sodium erythorbate, tea polyphenols, rosemary extract, ginger extract, sugar alcohols, amino acids, or a combination thereof.

In certain embodiments of the medicament delivery device, in the liquid formulation composition, the content of the surfactant is in the range from about 0.1 wt % to about 25.0 wt %, the content of the solvent is in the range from about 58.0 wt % to about 99.878 wt %, the content of the bacteriostatic agent is in the range from about 0.001 wt % to about 2.0 wt %, the content of the flavoring agent is in the range from about 0.01 wt % to about 5.0 wt %, the content of the stabilizer is in the range from about 0.01 wt % to about 5.0 wt %, and the content of the antioxidant is in the range from about 0.001 wt % to 5.0 wt %. In certain embodiments of the medicament delivery device, the content of the active pharmaceutical ingredient is in the range from about 0.001 wt % to about 5.0 wt %.

In yet another aspect, the invention generally relates to a method for preparing a liquid formulation composition. The method includes: (S1) dissolving or dispersing a surfactant in a solvent to form a solution or a stable suspension; and (S2) adjusting the solution or a stable suspension to form a liquid formulation composition characterized by a surface tension of less than about 60 mN/m and a pH value from about 5.0 to about 7.4.

In certain embodiments of the method, the surfactant includes one of natural phospholipid, sterol, pulmonary surfactant, stearic acid, oleic acid, lauric acid, benzalkonium chloride, benzalkonium bromide, cetrimide, sorbitan fatty acid, polysorbate, polyoxyethylene stearate, polyoxyethylene-fatty alcohol ether, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof.

In certain embodiments of the method, the surfactant includes one of lecithin, sterol, pulmonary surfactant, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof; and the solvent thereof is one of water, ethanol, glycerol, medical silicone oil, edible vegetable oil, or a combination thereof.

In certain embodiments of the method, in the liquid formulation composition, the content of the surfactant is in the range from about 0.0001 wt % to about 25.0 wt %, and the content of the solvent is in the range from about 75.0 wt % to about 99.9999 wt %.

In certain embodiments of the method, in step (S2), an active pharmaceutical ingredient is uniformly mixed with the surfactant and the solvent, wherein the active pharmaceutical ingredient includes one of medicines for treating rhinitis, sinusitis, lower respiratory tract inflammation, otitis media, otitis externa, xerostomia, xerophthalmia, xeromycteria, or a combination thereof.

Any suitable active pharmaceutical ingredients may be utilized, for example, one of cortisone, hydrocortisone, beclomethasone, triamcinolone acetonide, mometasone, dexamethasone, fluocinolone acetonide, budesonide, fluticasone, ephedrine hydrochloride, xylometazoline hydrochloride, levocabastine hydrochloride, azelastine hydrochloride, fructus xanthii, dandelion, radix scutellariae, bitter gourd, herba ephedrae, flos magnoliae, herba asari, radix angelicae dahuricae, rhizome acori tatarinowii, catechu, Longjing tea, cortex phellodendroni, ofloxacin, levofloxacin, norfloxacin, lomefloxacin, tosufloxacin, sparfloxacin, roxithromycin, chloromycetin, penicillin, clindamycin, nitrofurazone, amoxicillin, ampicillin, clavulanate potassium, cefaclor, cefixime, cefdinir, cephradine, cephalexin, cefpodoxime, cefuroxime axetil, cefprozil, azithromycin, minocycline, acetyl midecamycin, acetylspiramycin, metronidazole, musk, potassium aluminium sulfate anhydrous, calamine, borneol, cochineal, cacumen platycladi, echinacea root, baptisia tinctoria root, D-panthenol, glycerin, hyaluronic acid, butanediol, polyethylene glycol, propanediol, hexanediol, xylitol, sorbitol, or a combination thereof.

In certain embodiments of the method, in the liquid formulation composition, the content of the surfactant is in the range from about 0.0001 wt % to about 25.0 wt %, the content of the solvent is in the range from about 70.0 wt % to about 99.9989 wt %, and the content of the active pharmaceutical ingredient is in the range from about 0.001 wt % to about 5.0 wt %.

In certain embodiments, the method further includes the step of dissolving or dispersing one of bacteriostatic agent, flavoring agent, stabilizer, antioxidant, or a combination thereof in the solvent.

In certain embodiments of the method, in the liquid formulation composition, the content of the surfactant is in the range from about 0.0001 wt % to about 25.0 wt %, the content of the solvent is in the range from about 63.0 wt % to about 99.9879 wt %, the content of the bacteriostatic agent is in the range from about 0.001 wt % to about 2.0 wt %, the content of the flavoring agent is in the range from about 0.01 wt % to about 5.0 wt %, and the content of the antioxidant is in the range from about 0.001 wt % to about 5.0 wt %. In certain embodiments, the content of the surfactant is in the range from about 0.0001 wt % to about 25.0 wt %, the content of the solvent is in the range from about 58.0 wt % to about 99.9869 wt %, the content of the bacteriostatic agent is in the range from about 0.001 wt % to about 2.0 wt %, the content of the flavoring agent is in the range from about 0.01 wt % to about 5.0 wt %, and the content of the antioxidant is in the range from about 0.001 wt % to about 5.0 wt %, the content of the pharmaceutical ingredient in the range from about 0.001 wt % to about 5.0 wt %.

In certain embodiments of the method, the bacteriostatic agent includes one of parabens or its salts, benzoic acid or its salts, benzyl alcohol, phenylethanol, phenylacetic acid, phenoxyethanol, lauric acid monoglyceride, chlorobutanol, sorbic acid or its salts, calcium propionate, sodium propionate, dehydroacetic acid or its salts thereof, sodium diacetate, benzalkonium chloride, benzalkonium bromide, cetrimide, chlorhexidine acetate, propanediol, carbon dioxide, nisin, natamycin, momordicin, thimerosal, mercuric nitrate, or a combination thereof.

In certain embodiments of the method, the flavoring agent includes one of menthol, borneol, lemon oil, patchouli oil, cinnamon oil, jujube tincture, vanillin, peppermint oil, rose oil, eucalyptus oil, spearmint oil, eugenol, citral, jasmine extract, chrysanthemum extract, osmanthus extract, benzyl alcohol, phenylethanol, terpineol, methyl cyclopentenolone, α-amyl cinnamic aldehyde, butyric acid, hexanoic acid, isoamyl acetate, benzyl acetate, linalyl acetate, ethyl propionate, ethyl butyrate, isoamyl butyrate, benzyl butyrate, isoamyl isovalerate, ethyl hexanoate, ethyl heptanoate, ethyl lactate, allyl hexanoate, γ-nonalactone, ethyl maltol, allyl cyclohexyl propionate, maltol, γ-undecalactone, raspberry ketone, benzyl propionate, butyl butyrate, ethyl isovalerate, ethyl formate, benzyl benzoate, methyl pyrazine, 2,3-dimethyl pyrazine, trimethyl pyrazine, 2-acetyl pyrazine, 4-methyl-5-(β-hydroxyethyl) thiazole, 2-acetyl thiazole, 2,3,5,6-tetramethyl pyrazine, hexadecanal, ethyl vanillin, hydroxyl citronellal, or a combination thereof.

In certain embodiments of the method, the stabilizer includes one of lecithin, poloxamer, saponin, tannin, glycerin fatty acid ester, sucrose fatty acid ester, propanediol fatty acid ester, cholesterol, cholesterol ester, polyethylene glycol, cellulose or its derivatives, dextrin, Arabic gum, tragacanth gum, pectin cellulose cheese, gelatin, alginic acid, or a combination thereof.

In certain embodiments of the method, the antioxidant includes one of tert-butyl hydroxy anisole, butylated hydroxytoluene, tert-butyl hydroquinone, propyl gallate, ascorbyl palmitate, dilauryl thiodipropionate, 4-hexyl resorcinol, tocopherol (vitamin E), L-ascorbic acid, D-sodium erythorbate, tea polyphenols, rosemary extract, ginger extract, sugar alcohols, amino acids, or a combination thereof.

In yet another aspect, the invention generally relates to a method for preparing a liquid formulation composition. The method includes: (S1) dissolving or dispersing a surfactant in a solvent with an ultrasound of about 40 KHz to about 60 KHz for about 1 minute to about 3 minutes; and (S2) uniformly mixing an active pharmaceutical ingredient, the surfactant and a solvent under a stirring condition characterized by a rotational speed of more than 3000 rpm to form a liquid formulation composition characterized by a surface tension of less than about 60 mN/m and an absolute value of zeta potential of greater than about 15 mV.

In certain embodiments, the method further includes, after step (S2), ultrasonically crushing or high-pressure homogenizing the liquid formulation composition so as to form liquid particles with the volume average particle size in the range from about 50 nm to about 500 nm.

In certain embodiments of the method, in the liquid formulation composition, the content of the surfactant is in the range from about 0.1 wt % to about 25.0 wt %, and the content of the solvent is in the range from about 75.0 wt % to about 99.9 wt %.

In certain embodiments, the method further includes the step of dispersing one of bacteriostatic agent, flavoring agent, stabilizer, antioxidant, or a combination thereof in the solvent. In the liquid formulation composition, the content of the surfactant is in the range from about 0.1 wt % to about 25.0 wt %, the content of the solvent is in the range from about 58.0 wt % to about 99.878 wt %, the content of the bacteriostatic agent is in the range from about 0.001 wt % to about 2.0 wt %, the content of the flavoring agent is in the range from about 0.01 wt % to about 5.0 wt %, the content of the stabilizer is in the range from about 0.01 wt % to about 5.0 wt %, and the content of the antioxidant is in the range from about 0.001 wt % to about 5.0 wt %.

In certain embodiments of the method, the bacteriostatic agent includes one of parabens or its salts, benzoic acid or its salts, benzyl alcohol, phenylethanol, phenylacetic acid, phenoxyethanol, lauric acid monoglyceride, chlorobutanol, sorbic acid or its salts, calcium propionate, sodium propionate, dehydroacetic acid or its salts, sodium diacetate, benzalkonium chloride, benzalkonium bromide, cetrimide, chlorhexidine acetate, propanediol, carbon dioxide, nisin, natamycin, momordicin, thimerosal, mercuric nitrate, or a combination thereof.

In certain embodiments of the method, the flavoring agent thereof includes one of menthol, borneol, lemon oil, patchouli oil, cinnamon oil, jujube tincture, vanillin, peppermint oil, rose oil, eucalyptus oil, spearmint oil, eugenol, citral, jasmine extract, chrysanthemum extract, osmanthus extract, benzyl alcohol, phenylethanol, terpineol, methyl cyclopentenolone, α-amyl cinnamic aldehyde, butyric acid, hexanoic acid, isoamyl acetate, benzyl acetate, linalyl acetate, ethyl propionate, ethyl butyrate, isoamyl butyrate, benzyl butyrate, isoamyl isovalerate, ethyl hexanoate, ethyl heptanoate, ethyl lactate, allyl hexanoate, γ-nonalactone, ethyl maltol, allyl cyclohexyl propionate, maltol, γ-undecalactone, raspberry ketone, benzyl propionate, butyl butyrate, ethyl isovalerate, ethyl formate, benzyl benzoate, methyl pyrazine, 2,3-dimethyl pyrazine, trimethyl pyrazine, 2-acetyl pyrazine, 4-methyl-5-(β-hydroxyethyl) thiazole, 2-acetyl thiazole, 2,3,5,6-tetramethyl pyrazine, hexadecanal, ethyl vanillin, hydroxyl citronellal, or a combination thereof.

In certain embodiments of the method, the stabilizer includes one of lecithin, poloxamer, saponin, tannin, glycerin fatty acid ester, sucrose fatty acid ester, propanediol fatty acid ester, cholesterol, cholesterol ester, polyethylene glycol, cellulose or its derivatives, dextrin, Arabic gum, tragacanth gum, pectin cellulose cheese, gelatin, alginic acid, or a combination thereof.

In certain embodiments of the method, the antioxidant includes one of tert-butyl hydroxy anisole, butylated hydroxytoluene, tert-butyl hydroquinone, propyl gallate, ascorbyl palmitate, dilauryl thiodipropionate, 4-hexyl resorcinol, tocopherol, L-ascorbic acid, D-sodium erythorbate, tea polyphenols, rosemary extract, ginger extract, sugar alcohols, amino acids, or a combination thereof.

Any suitable surfactant(s) may be utilized. In certain embodiments of the method, the surfactant includes one of natural phospholipid, sterol, pulmonary surfactant, stearic acid, oleic acid, lauric acid, benzalkonium chloride, benzalkonium bromide, cetrimide, sorbitan fatty acid, polysorbate, polyoxyethylene stearate, polyoxyethylene-fatty alcohol ether, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof.

In certain embodiments of the method, the surfactant includes one of lecithin, sterol, pulmonary surfactant, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof.

In certain embodiments, the invention provides a solid formulation composition obtained by removing the solvent from the liquid formulation composition of the invention.

In yet another aspect, the invention generally relates to a method for preparing the liquid formulation composition. The method includes: (S1) dissolving or dispersing a surfactant in a solvent with an ultrasound of about 40 KHz to about 60 KHz for about 1 minute to about 3 minutes; and (S2) uniformly mixing an active pharmaceutical ingredient, the surfactant and a solvent under a stirring condition characterized by a rotational speed of more than 3000 rpm to form a liquid formulation composition in the form of an emulsion. The liquid formulation composition includes a solvent and, dispersed therein, liquid particles including a surfactant. The volume average particle size of the liquid particles is less than about 100 μm. The liquid formulation composition is characterized by a surface tension of less than about 60 mN/m and an absolute value of zeta potential of more than about 15 mV. The active pharmaceutical ingredient is selected from one of medicines for treating rhinitis, sinusitis, lower respiratory tract inflammation, otitis media, otitis externa, xerostomia, xerophthalmia, xeromycteria, or a combination thereof.

In certain embodiments, the method further includes, after step (S2), ultrasonically crushing or high-pressure homogenizing the liquid formulation composition so as to form liquid particles with the volume average particle size in the range from about 50 to about 500 nm.

In certain embodiments of the method, the surfactant is in the range from about 0.1 wt % to about 25.0 wt %; the solvent is in the range from about 70.0 wt % to about 99.899 wt %; and the active pharmaceutical ingredient is in the range from about 0.001 wt % to about 5.0 wt %.

In certain embodiments, the method further includes, the step of dispersing one of bacteriostatic agent, flavoring agent, stabilizer, antioxidant, or a combination thereof in the solvent, wherein in the liquid formulation composition, the surfactant is in the range from about 0.1 wt % to about 25.0 wt %, the solvent is in the range from about 53.0 wt % to about 99.878 wt %, the bacteriostatic agent is in the range from about 0.001 wt % to about 2.0 wt %, the flavoring agent is in the range from about 0.01 wt % to about 5.0 wt %, the adding amount of the stabilizer is in the range from about 0.01 wt % to about 5.0 wt %, the antioxidant is in the range from about 0.001 wt % to about 5.0 wt %, and the active pharmaceutical ingredient is in the range from about 0.001 wt % to about 5.0 wt %.

In certain embodiments of the method, the bacteriostatic agent includes one of parabens or its salts, benzoic acid or its salts, benzyl alcohol, phenylethanol, phenylacetic acid, phenoxyethanol, lauric acid monoglyceride, chlorobutanol, sorbic acid or its salts, calcium propionate, sodium propionate, dehydroacetic acid or its salts thereof, sodium diacetate, benzalkonium chloride, benzalkonium bromide, cetrimide, chlorhexidine acetate, propanediol, carbon dioxide, nisin, natamycin, momordicin, thimerosal, mercuric nitrate, or a combination thereof.

In certain embodiments of the method, the flavoring agent includes one of menthol, borneol, lemon oil, patchouli oil, cinnamon oil, jujube tincture, vanillin, peppermint oil, rose oil, eucalyptus oil, spearmint oil, eugenol, citral, jasmine extract, chrysanthemum extract, osmanthus extract, benzyl alcohol, phenylethanol, terpineol, methyl cyclopentenolone, α-amyl cinnamic aldehyde, butyric acid, hexanoic acid, isoamyl acetate, benzyl acetate, linalyl acetate, ethyl propionate, ethyl butyrate, isoamyl butyrate, benzyl butyrate, isoamyl isovalerate, ethyl hexanoate, ethyl heptanoate, ethyl lactate, allyl hexanoate, γ-nonalactone, ethyl maltol, allyl cyclohexyl propionate, maltol, γ-undecalactone, raspberry ketone, benzyl propionate, butyl butyrate, ethyl isovalerate, ethyl formate, benzyl benzoate, methyl pyrazine, 2,3-dimethyl pyrazine, trimethyl pyrazine, 2-acetyl pyrazine, 4-methyl-5-(β-hydroxyethyl) thiazole, 2-acetyl thiazole, 2,3,5,6-tetramethyl pyrazine, hexadecanal, ethyl vanillin, hydroxyl citronellal, or a combination thereof.

In certain embodiments of the method, the stabilizer includes one of lecithin, poloxamer, saponin, tannin, glycerin fatty acid ester, sucrose fatty acid ester, propanediol fatty acid ester, cholesterol, cholesterol ester, polyethylene glycol, cellulose or its derivatives, dextrin, Arabic gum, tragacanth gum, pectin cellulose cheese, gelatin, alginic acid, or a combination thereof; and In certain embodiments of the method, the antioxidant includes one of tert-butyl hydroxy anisole, butylated hydroxytoluene, tert-butyl hydroquinone, propyl gallate, ascorbyl palmitate, dilauryl thiodipropionate, 4-hexyl resorcinol, tocopherol (vitamin E), L-ascorbic acid, D-sodium erythorbate, tea polyphenols, rosemary extract, ginger extract, sugar alcohols, amino acids, or a combination thereof.

In certain embodiments of the method, the surfactant includes one of natural phospholipid, sterol, pulmonary surfactant, stearic acid, oleic acid, lauric acid, benzalkonium chloride, benzalkonium bromide, cetrimide, sorbitan fatty acid, polysorbate, polyoxyethylene stearate, polyoxyethylene-fatty alcohol ether, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof the solvent is one of water, ethanol, glycerol, medical silicone oil and edible vegetable oil, or a combination thereof and the active pharmaceutical ingredient includes one of cortisone, hydrocortisone, beclomethasone, triamcinolone acetonide, mometasone, dexamethasone, fluocinolone acetonide, budesonide, fluticasone, ephedrine hydrochloride, xylometazoline hydrochloride, levocabastine hydrochloride, azelastine hydrochloride, fructus xanthii, dandelion, radix scutellariae, bitter gourd, herba ephedrae, flos magnoliae, herba asari, radix angelicae dahuricae, rhizome acori tatarinowii, catechu, Longjing tea, cortex phellodendri, ofloxacin, levofloxacin, norfloxacin, lomefloxacin, tosufloxacin, sparfloxacin, roxithromycin, chloromycetin, penicillin, clindamycin, nitrofurazone, amoxicillin, ampicillin, clavulanate potassium, cefaclor, cefixime, cefdinir, cephradine, cephalexin, cefpodoxime, cefuroxime axetil, cefprozil, azithromycin, minocycline, acetyl midecamycin, acetylspiramycin, metronidazole, musk, potassium aluminium sulfate anhydrous, calamine, borneol, cochineal, cacumen platycladi, echinacea root, baptisia tinctoria root, D-panthenol, glycerin, hyaluronic acid, butanediol, polyethylene glycol, propanediol, hexanediol, xylitol, sorbitol, or a combination thereof.

In yet another aspect, the invention generally relates to a method for preparing a medicament delivery device. The method includes: (S1) dissolving or dispersing a surfactant in a solvent to form a solution or a stable suspension; and (S2) adjusting the solution to form a liquid formulation composition characterized by a surface tension of less than about 60 mN/m and a pH value from about 5.0 to about 7.4, and (S3) filling the liquid formulation composition into a containment vessel.

In certain embodiments of the method, the containment vessel is configured to function as a sprayer, allowing controlled spraying of the liquid formulation composition out of the outlet.

In certain embodiments of the method, the containment vessel is configured to function as a dropping device, allowing controlled dropping of the liquid formulation composition out of the outlet.

In certain embodiments of the method, the buffer is added to keep the pH value of solution in the range of about 5.0 to about 7.4.

In certain embodiments of the method, the surfactant includes one of natural phospholipid, sterol, pulmonary surfactant, stearic acid, oleic acid, lauric acid, benzalkonium chloride, benzalkonium bromide, cetrimide, sorbitan fatty acid, polysorbate, polyoxyethylene stearate, polyoxyethylene-fatty alcohol ether, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof.

In certain embodiments of the method, the surfactant includes one of lecithin, sterol, pulmonary surfactant, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof; and the solvent thereof is one of water, ethanol, glycerol, medical silicone oil, edible vegetable oil, or a combination thereof.

In certain embodiments of the method, in the liquid formulation composition, the content of the surfactant is in the range from about 0.0001 wt % to about 25.0 wt %, and the content of the solvent is in the range from about 75.0 wt % to about 99.9999 wt %.

In certain embodiments of the method, in step (S2), an active pharmaceutical ingredient is uniformly mixed with the surfactant and the solvent, wherein the active pharmaceutical ingredient includes one of medicines for treating rhinitis, sinusitis, lower respiratory tract inflammation, otitis media, otitis externa, xerostomia, xerophthalmia, xeromycteria, or a combination thereof.

Any suitable active pharmaceutical ingredients may be utilized, for example, one of cortisone, hydrocortisone, beclomethasone, triamcinolone acetonide, mometasone, dexamethasone, fluocinolone acetonide, budesonide, fluticasone, ephedrine hydrochloride, xylometazoline hydrochloride, levocabastine hydrochloride, azelastine hydrochloride, fructus xanthii, dandelion, radix scutellariae, bitter gourd, herba ephedrae, flos magnoliae, herba asari, radix angelicae dahuricae, rhizome acori tatarinowii, catechu, Longjing tea, cortex phellodendroni, ofloxacin, levofloxacin, norfloxacin, lomefloxacin, tosufloxacin, sparfloxacin, roxithromycin, chloromycetin, penicillin, clindamycin, nitrofurazone, amoxicillin, ampicillin, clavulanate potassium, cefaclor, cefixime, cefdinir, cephradine, cephalexin, cefpodoxime, cefuroxime axetil, cefprozil, azithromycin, minocycline, acetyl midecamycin, acetylspiramycin, metronidazole, musk, potassium aluminium sulfate anhydrous, calamine, borneol, cochineal, cacumen platycladi, echinacea root, baptisia tinctoria root, D-panthenol, glycerin, hyaluronic acid, butanediol, polyethylene glycol, propanediol, hexanediol, xylitol, sorbitol, or a combination thereof.

In certain embodiments of the method, in the liquid formulation composition, the content of the surfactant is in the range from about 0.0001 wt % to about 25.0 wt %, the content of the solvent is in the range from about 70.0 wt % to about 99.9989 wt %, and the content of the active pharmaceutical ingredient is in the range from about 0.001 wt % to about 5.0 wt %.

In certain embodiments, the method further includes the step of dispersing one of bacteriostatic agent, flavoring agent, stabilizer, antioxidant, or a combination thereof in the solvent.

In certain embodiments of the method, in the liquid formulation composition, the content of the surfactant is in the range from about 0.0001 wt % to about 25.0 wt %, the content of the solvent is in the range from about 58.0 wt % to about 99.9689 wt %, the content of the bacteriostatic agent is in the range from about 0.001 wt % to about 2.0 wt %, the content of the flavoring agent is in the range from about 0.01 wt % to about 5.0 wt %, and the content of the antioxidant is in the range from about 0.001 wt % to about 5.0 wt %. In certain embodiments, the content of the pharmaceutical ingredient in the range from about 0.001 wt % to about 5.0 wt %.

In certain embodiments of the method, the bacteriostatic agent includes one of parabens or its salts, benzoic acid or its salts, benzyl alcohol, phenylethanol, phenylacetic acid, phenoxyethanol, lauric acid monoglyceride, chlorobutanol, sorbic acid or its salts, calcium propionate, sodium propionate, dehydroacetic acid or its salts thereof, sodium diacetate, benzalkonium chloride, benzalkonium bromide, cetrimide, chlorhexidine acetate, propanediol, carbon dioxide, nisin, natamycin, momordicin, thimerosal, mercuric nitrate, or a combination thereof.

In certain embodiments of the method, the flavoring agent includes one of menthol, borneol, lemon oil, patchouli oil, cinnamon oil, jujube tincture, vanillin, peppermint oil, rose oil, eucalyptus oil, spearmint oil, eugenol, citral, jasmine extract, chrysanthemum extract, osmanthus extract, benzyl alcohol, phenylethanol, terpineol, methyl cyclopentenolone, α-amyl cinnamic aldehyde, butyric acid, hexanoic acid, isoamyl acetate, benzyl acetate, linalyl acetate, ethyl propionate, ethyl butyrate, isoamyl butyrate, benzyl butyrate, isoamyl isovalerate, ethyl hexanoate, ethyl heptanoate, ethyl lactate, allyl hexanoate, γ-nonalactone, ethyl maltol, allyl cyclohexyl propionate, maltol, γ-undecalactone, raspberry ketone, benzyl propionate, butyl butyrate, ethyl isovalerate, ethyl formate, benzyl benzoate, methyl pyrazine, 2,3-dimethyl pyrazine, trimethyl pyrazine, 2-acetyl pyrazine, 4-methyl-5-(β-hydroxyethyl) thiazole, 2-acetyl thiazole, 2,3,5,6-tetramethyl pyrazine, hexadecanal, ethyl vanillin, hydroxyl citronellal, or a combination thereof.

In certain embodiments of the method, the stabilizer includes one of lecithin, poloxamer, saponin, tannin, glycerin fatty acid ester, sucrose fatty acid ester, propanediol fatty acid ester, cholesterol, cholesterol ester, polyethylene glycol, cellulose or its derivatives, dextrin, Arabic gum, tragacanth gum, pectin cellulose cheese, gelatin, alginic acid, or a combination thereof.

In certain embodiments of the method, the antioxidant includes one of tert-butyl hydroxy anisole, butylated hydroxytoluene, tert-butyl hydroquinone, propyl gallate, ascorbyl palmitate, dilauryl thiodipropionate, 4-hexyl resorcinol, tocopherol (vitamin E), L-ascorbic acid, D-sodium erythorbate, tea polyphenols, rosemary extract, ginger extract, sugar alcohols, amino acids, or a combination thereof.

In yet another aspect, the invention generally relates to a method for preparing the medicament delivery device. The method include: (S1) dissolving or dispersing a surfactant in a solvent with an ultrasound of about 40 KHz to about 60 KHz for about 1 minute to about 3 minutes; and (S2) uniformly mixing the surfactant with a solvent under a stirring condition characterized by a rotational speed of more than 3000 rpm to form a liquid formulation. The liquid formulation composition is an emulsion and includes a solvent and, dispersed therein, liquid particles including a surfactant. The volume average particle size of the liquid particles is less than about 100 μm. The liquid formulation composition is characterized by a surface tension of less than about 60 mN/m and an absolute value of zeta potential of more than about 15 mV; and (S3) filling the liquid formulation composition into a containment vessel.

In certain embodiments of the method, the containment vessel is configured to function as a sprayer, allowing controlled spraying of the liquid formulation composition out of the outlet.

In certain embodiments of the method, the containment vessel is configured to function as a dropping device, allowing controlled dropping of the liquid formulation composition out of the outlet.

In certain embodiments, the method further includes, after step (S2), ultrasonically crushing or high-pressure homogenizing the liquid formulation composition so as to form liquid particles with the volume average particle size in the range from about 50 nm to about 500 nm.

In certain embodiments of the method, the surfactant includes one of natural phospholipid, sterol, pulmonary surfactant, stearic acid, oleic acid, lauric acid, benzalkonium chloride, benzalkonium bromide, cetrimide, sorbitan fatty acid, polysorbate, polyoxyethylene stearate, polyoxyethylene-fatty alcohol ether, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof.

In certain embodiments of the method, the surfactant includes one of lecithin, sterol, pulmonary surfactant, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof; and the solvent thereof is one of water, ethanol, glycerol, medical silicone oil, edible vegetable oil, or a combination thereof.

In certain embodiments of the method, in the liquid formulation composition, the content of the surfactant is in the range from about 0.1 wt % to about 25.0 wt %, and the content of the solvent is in the range from about 75.0 wt % to about 99.9 wt %.

In certain embodiments, the method further includes the step of dispersing one of bacteriostatic agent, flavoring agent, stabilizer, antioxidant, or a combination thereof in the solvent.

In certain embodiments of the method, in the liquid formulation composition, the content of the surfactant is in the range from about 0.1 wt % to about 25.0 wt %, the content of the solvent is in the range from about 58.0 wt % to about 99.878 wt %, the content of the bacteriostatic agent is in the range from about 0.001 wt % to about 2.0 wt %, the content of the flavoring agent is in the range from about 0.01 wt % to about 5.0 wt %, the content of the stabilizer is in the range from about 0.01 wt % to about 5.0 wt %, and the content of the antioxidant is in the range from about 0.001 wt % to about 5.0 wt %.

In certain embodiments of the method, the bacteriostatic agent includes one of parabens or its salts, benzoic acid or its salts, benzyl alcohol, phenylethanol, phenylacetic acid, phenoxyethanol, lauric acid monoglyceride, chlorobutanol, sorbic acid or its salts, calcium propionate, sodium propionate, dehydroacetic acid or its salts thereof, sodium diacetate, benzalkonium chloride, benzalkonium bromide, cetrimide, chlorhexidine acetate, propanediol, carbon dioxide, nisin, natamycin, momordicin, thimerosal, mercuric nitrate, or a combination thereof.

In certain embodiments of the method, the flavoring agent includes one of menthol, borneol, lemon oil, patchouli oil, cinnamon oil, jujube tincture, vanillin, peppermint oil, rose oil, eucalyptus oil, spearmint oil, eugenol, citral, jasmine extract, chrysanthemum extract, osmanthus extract, benzyl alcohol, phenylethanol, terpineol, methyl cyclopentenolone, α-amyl cinnamic aldehyde, butyric acid, hexanoic acid, isoamyl acetate, benzyl acetate, linalyl acetate, ethyl propionate, ethyl butyrate, isoamyl butyrate, benzyl butyrate, isoamyl isovalerate, ethyl hexanoate, ethyl heptanoate, ethyl lactate, allyl hexanoate, γ-nonalactone, ethyl maltol, allyl cyclohexyl propionate, maltol, γ-undecalactone, raspberry ketone, benzyl propionate, butyl butyrate, ethyl isovalerate, ethyl formate, benzyl benzoate, methyl pyrazine, 2,3-dimethyl pyrazine, trimethyl pyrazine, 2-acetyl pyrazine, 4-methyl-5-(β-hydroxyethyl) thiazole, 2-acetyl thiazole, 2,3,5,6-tetramethyl pyrazine, hexadecanal, ethyl vanillin, hydroxyl citronellal, or a combination thereof.

In certain embodiments of the method, the stabilizer includes one of lecithin, poloxamer, saponin, tannin, glycerin fatty acid ester, sucrose fatty acid ester, propanediol fatty acid ester, cholesterol, cholesterol ester, polyethylene glycol, cellulose or its derivatives, dextrin, Arabic gum, tragacanth gum, pectin cellulose cheese, gelatin, alginic acid, or a combination thereof.

In certain embodiments of the method, the antioxidant includes one of tert-butyl hydroxy anisole, butylated hydroxytoluene, tert-butyl hydroquinone, propyl gallate, ascorbyl palmitate, dilauryl thiodipropionate, 4-hexyl resorcinol, tocopherol (vitamin E), L-ascorbic acid, D-sodium erythorbate, tea polyphenols, rosemary extract, ginger extract, sugar alcohols, amino acids, or a combination thereof.

In certain embodiments of the method, in step (S2), an active pharmaceutical ingredient is uniformly mixed with the surfactant and the solvent, wherein the active pharmaceutical ingredient includes one of medicines for treating rhinitis, sinusitis, lower respiratory tract inflammation, otitis media, otitis externa, xerostomia, xerophthalmia, xeromycteria, or a combination thereof.

In certain embodiments of the method, the active pharmaceutical ingredient includes one of cortisone, hydrocortisone, beclomethasone, triamcinolone acetonide, mometasone, dexamethasone, fluocinolone acetonide, budesonide, fluticasone, ephedrine hydrochloride, xylometazoline hydrochloride, levocabastine hydrochloride, azelastine hydrochloride, fructus xanthii, dandelion, radix scutellariae, bitter gourd, herba ephedrae, flos magnoliae, herba asari, radix angelicae dahuricae, rhizome acori tatarinowii, catechu, Longjing tea, cortex phellodendroni, ofloxacin, levofloxacin, norfloxacin, lomefloxacin, tosufloxacin, sparfloxacin, roxithromycin, chloromycetin, penicillin, clindamycin, nitrofurazone, amoxicillin, ampicillin, clavulanate potassium, cefaclor, cefixime, cefdinir, cephradine, cephalexin, cefpodoxime, cefuroxime axetil, cefprozil, azithromycin, minocycline, acetyl midecamycin, acetylspiramycin, metronidazole, musk, potassium aluminium sulfate anhydrous, calamine, borneol, cochineal, cacumen platycladi, Echinacea root, baptisia tinctoria root, D-panthenol, glycerin, hyaluronic acid, butanediol, polyethylene glycol, propanediol, hexanediol, xylitol, sorbitol, or a combination thereof.

In certain embodiments of the method, in the liquid formulation composition the content of the surfactant is in the range from about 0.1 wt % to about 25.0 wt %, the content of the solvent is in the range from about 53.0 wt % to about 99.877 wt %, the content of the bacteriostatic agent is in the range from about 0.001 wt % to about 2.0 wt %, the content of the flavoring agent is in the range from about 0.01 wt % to about 5.0 wt %, the content of the stabilizer is in the range from about 0.01 wt % to about 5.0 wt %, the content of the antioxidant is in the range from about 0.001 wt % to about 5.0 wt %, and the content of the active pharmaceutical ingredient is in the range from about 0.001 wt % to about 5.0 wt %.

In certain embodiments of the method, the containment vessel is an anti-contamination sprayer or an anti-contamination dropping device.

In yet another aspect, the invention generally relates to a method for treating, reducing, or preventing one or more diseases or disorders. The method includes administering to a subject in need thereof a liquid formulation composition disclosed herein, in an amount effective to treat, prevent, or reduce one or more diseases or disorders selected from rhinitis, sinusitis, lower respiratory tract inflammation, otitis media, otitis externa, xerostomia, xerophthalmia and xeromycteria.

In certain embodiments of the method, the one or more diseases or disorders include otitis media. In certain embodiments of the method, the one or more diseases or disorders include otitis externa. In certain embodiments of the method, the one or more diseases or disorders include rhinitis. In certain embodiments of the method, the one or more diseases or disorders include sinusitis. In certain embodiments of the method, the one or more diseases or disorders include xerostomia. In certain embodiments of the method, the one or more diseases or disorders include xerophthalmia. In certain embodiments of the method, the one or more diseases or disorders include xeromycteria. In certain embodiments of the method, the one or more diseases or disorders include lower respiratory tract inflammation.

In yet another aspect, the invention generally relates to a method for treating, reducing, or preventing one or more diseases or disorders. The method includes administering to a subject in need thereof a liquid formulation composition, using the medicament delivery device disclosed herein, in an amount effective to treat, prevent, or reduce one or more diseases or disorders selected from rhinitis, sinusitis, lower respiratory tract inflammation, otitis media, otitis externa, xerostomia, xerophthalmia and xeromycteria.

In certain embodiments of the method, the one or more diseases or disorders include otitis media. In certain embodiments of the method, the one or more diseases or disorders include otitis externa. In certain embodiments of the method, the one or more diseases or disorders include rhinitis. In certain embodiments of the method, the one or more diseases or disorders include sinusitis. In certain embodiments of the method, the one or more diseases or disorders include xerostomia. In certain embodiments of the method, the one or more diseases or disorders include xerophthalmia. In certain embodiments of the method, the one or more diseases or disorders include xeromycteria. In certain embodiments of the method, the one or more diseases or disorders include lower respiratory tract inflammation.

In yet another aspect, the invention generally relates to a method for treatment of otitis media using the liquid formulation composition of the invention.

In yet another aspect, the invention generally relates to a method for treatment of otitis externa using the liquid formulation composition of the invention.

In yet another aspect, the invention generally relates to a method for treatment of rhinitis using the liquid formulation composition of the invention.

In yet another aspect, the invention generally relates to a method for treatment of sinusitis using the liquid formulation composition of the invention.

In yet another aspect, the invention generally relates to a method for treatment of xerostomia using the liquid formulation composition of the invention.

In yet another aspect, the invention generally relates to a method for treatment of xerophthalmia using the liquid formulation composition of the invention.

In yet another aspect, the invention generally relates to a method for treatment of xeromycteria using the liquid formulation composition of the invention.

In yet another aspect, the invention generally relates to a method for treatment of lower respiratory tract inflammation using the liquid formulation composition of the invention.

In yet another aspect, the invention generally relates to a method for treatment of otitis media using the medicament delivery device of the invention.

In yet another aspect, the invention generally relates to a method for treatment of otitis externa using the medicament delivery device of the invention.

In yet another aspect, the invention generally relates to a method for treatment of rhinitis using the medicament delivery device of the invention.

In yet another aspect, the invention generally relates to a method for treatment of sinusitis using the medicament delivery device of the invention.

In yet another aspect, the invention generally relates to a method for treatment of xerostomia using the medicament delivery device of the invention.

In yet another aspect, the invention generally relates to a method for treatment of xerophthalmia using the medicament delivery device of the invention.

In yet another aspect, the invention generally relates to a method for treatment of xeromycteria using the medicament delivery device of the invention.

In yet another aspect, the invention generally relates to a method for treatment of lower respiratory tract inflammation using the medicament delivery device of the invention.

For the liquid formulation compositions disclosed herein, the surface tension generally should be less than about 60 mN/m. As discussed herein, when the surface tension of the liquid formulation composition is less than about 60 mN/m, the surface tension Eustachian tube reduced and the surface tension of effusion at mucosa of Eustachian tube is also reduced, the effusion can flow out smoothly, the ear pressure can be reduced, and the symptoms of tinnitus and headache can be eliminated; and meanwhile, the risk of infection is reduced, the elimination of inflammation is promoted, and the healing is promoted.

According to the invention, in order to realize the treatment effect in a faster and better manner, preferably, the surface tension of the liquid formulation composition is less than about 40 mN/m, more preferably, the surface tension of the liquid formulation composition is less than about 30 mN/m, and most preferably, the surface tension of the liquid formulation composition is less than about 27 mN/m. The smaller surface tension of the liquid formulation composition is more conductive to reducing the surface tension of the effusion of the Eustachian tube and more conductive to outflow of the middle ear effusion.

It is noted, however, experiments show that the lesser surface tension of the liquid formulation composition can make the liquid formulation composition less stable, make the surfactant in the solvent easier to aggregate or even stratify or settle, potentially causing poor stability and less effective when used in the form of spray or drop.

The volume average particle size is defined as the particle size of a hypothetical particle population that has the same particle shape, the same total volume and the same number of particles as the particle population, and uniform particle size.

When the particle size of the liquid particles in the solvent meets the above conditions, the liquid particles can be dispersed in the solvent more stably.

To ensure that the liquid formulation composition disclosed herein has sufficient stability so as to allow the use of a liquid formulation composition in the form of spray or drop, the volume average particle size of the liquid particles is maintained less than about 100 μm, and more preferably, the volume average particle size of the liquid particles is less than about 10 μm or even less than about 6 μm.

In certain embodiments, the volume average particle size of the liquid particles is in the range from about 1 μm to about 100 μm, and more preferably, the volume average particle size of the liquid particles is in the range from about 1 μm to about 10 μm or even from about 1 μm to about 6 μm.

In certain embodiments, preferably, the volume average particle size of the liquid particles is in the range from about 50 nm to about 500 nm, and more preferably, the volume average particle size of the liquid particles is in the range from about 100 nm to about 500 nm or even from about 200 nm to about 400 nm. At this condition, the stability of the liquid particles in the solvent is increased.

In order to ensure that the liquid formulation composition disclosed herein has sufficient stability, on the premise of ensuring that the particle size is in the ranges above by the process, the relative contents of the surfactant, the solvent and other substances which are selectively added in the liquid formulation composition will affect zeta potential, and it is found that, when the absolute value of zeta potential of the liquid formulation composition disclosed herein is more than 15 mV, the liquid formulation composition has good stability.

As well known to those skilled in the art, the zeta potential which is also known as electric potential (ζ-potential) refers to potential on a shear plane. More preferably, the absolute value of zeta potential of the liquid formulation composition is more than 20 mV or even more than 40 mV. At this time, the liquid formulation composition has more desirable stability.

In certain embodiments of the invention, to improve the stability of the liquid formulation composition and simultaneously reduce the irritation to a user, the pH value of the liquid formulation composition is preferably in the range from about 5.0 to about 7.4 and more preferably in the range from about 6.0 to about 7.4.

In the invention, the adopted surfactant can be selected from various known and safe substances in the fields of medicines, foods and the like, for example, the surfactant is selected from, but not limited to, one of natural phospholipid, sterol, pulmonary surfactant, stearic acid, oleic acid, lauric acid, benzalkonium chloride, benzalkonium bromide, cetrimide, sorbitan fatty acid, polysorbate, polyoxyethylene stearate, polyoxyethylene-fatty alcohol ether, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof. In order to ensure the use safety of the liquid formulation composition disclosed herein, the surfactant preferably adopts substances with high safety and excellent activity, for example, the surfactant is selected from, but not limited to, one of lecithin, sterol, pulmonary surfactant, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof.

Studies report that in samples of patients with the secretory otitis media, the content of phospholipid representing a surfactant is obviously reduced in comparison with that of a healthy control group, and the difference has statistical significance ($p<0.01$), so that the situation confirms that the reduction of the surfactant in the patients with the secretory otitis media is mainly shown in the nasopharynx, the middle ear and part of the eustachian tube, further forces the increase of the open pressure of the eustachian tube and enables the compliance to be possible, causes the effusion in middle ear cavity and the retention of the effusion, and finally causes the secretory otitis media. When the above various substances (e.g., phospholipid) are taken as the surfactant, on the basis of realizing the purposes of the invention, the reduced ingredients (e.g., phospholipid) at nasopharynxes of patients with otitis media and rhinitis can be also supplemented to bring additional symptom reliefs.

For the formulation composition disclosed herein, particularly, when the surfactant adopts the above various substances, too high or too low pH can cause hydrolysis of the surfactant, and the stability of the formulation composition can be greatly reduced.

The above various substances are commercially available.

There is no particular limitation of the solvent in the liquid formulation composition disclosed herein, and the solvent can be one of water, ethanol, glycerol, medical silicone oil, edible vegetable oil, or a combination thereof. For example, the solvent in the invention is water.

According to the invention, the relative content of the solvent and the surfactant in the liquid formulation composition can change within a relatively large range, and as known to those skilled in the art, the different relative contents of the solvent and the surfactant can result in different surface tension and zeta potential of the liquid formulation composition. In the invention, only the surface tension and the zeta potential of the liquid formulation composition need to meet the requirements described above. The liquid formulation composition is prepared by those skilled in the art by adjusting the relative contents of the solvent and the surfactant to make the surface tension and the zeta potential of the liquid formulation composition within the range described above. Generally, against corresponding disease symptoms, after raw material ingredients required for the liquid formulation composition are determined, the adding amount of each raw material ingredient is continuously changed to enable the finally obtained liquid formulation composition to meet the conditions of the invention, and at this time, the adding amount of each raw material ingredient can be recorded. When the liquid formulation composition with the same composition is prepared subsequently, just based on the known adding amount of each raw material ingredient, the formulation can be directly prepared.

Preferably, in the liquid formulation composition, the content of the surfactant is in the range from about 0.1 wt % to about 25.0 wt %, and the content of the solvent is in the range from about 75.0 wt % to about 99.9 wt %. When the above surfactant adopts a variety of substances for matching and use, there is no limitation of the relative content of the various substances as long as the surface tension and the zeta potential of the whole liquid formulation composition meet the conditions described above.

In the invention, in order to better ensure the stability of the liquid formulation composition, prevent the occurrence of sedimentation and prolong the storage time, preferably, the liquid formulation composition disclosed herein further includes a stabilizer. The applied stabilizer includes, but not limited to well-known edible stabilizers by those skilled in the art, one of lecithin, poloxamer, saponin, tannin, glycerin fatty acid ester, sucrose fatty acid ester, propanediol fatty acid ester, cholesterol, cholesterol ester, polyethylene glycol, cellulose or its derivatives, dextrin, Arabic gum, tragacanth gum, pectin cellulose cheese, gelatin, alginic acid, or a combination thereof.

In the stabilizers that can be adopted, some substances, such as lecithin, poloxamer, cholesterol and cholesterol ester, are the same as the substances adopted by the surfactant. Each substance has better stability in the liquid formulation composition and can be simultaneously taken as the surfactant and the stabilizer by itself.

The amount of stabilizer in the liquid formulation composition can vary within a relatively large range, as long as the surface tension of the liquid formulation composition is ensured to be within the range described herein. Preferably, the content of the stabilizer is in the range from about 0.01 wt % to about 5.0 wt %.

To improve patient compliance, the liquid formulation composition can further include one or more flavoring agents, such as, but not limited to, one of menthol, borneol, lemon oil, patchouli oil, cinnamon oil, jujube tincture, vanillin, peppermint oil, rose oil, eucalyptus oil, spearmint oil, eugenol, citral, jasmine extract, chrysanthemum extract, osmanthus extract, benzyl alcohol, phenylethanol, terpineol, methyl cyclopentenolone, α-amyl cinnamic aldehyde, butyric acid, hexanoic acid, isoamyl acetate, benzyl acetate, linalyl acetate, ethyl propionate, ethyl butyrate, isoamyl butyrate, benzyl butyrate, isoamyl isovalerate, ethyl hexanoate, ethyl heptanoate, ethyl lactate, allyl hexanoate, γ-nonalactone, ethyl maltol, allyl cyclohexyl propionate, maltol, γ-undecalactone (peach aldehyde), raspberry ketone (raspberry ketone), benzyl propionate, butyl butyrate, ethyl isovalerate, ethyl formate, benzyl benzoate, methyl pyrazine, 2,3-dimethyl pyrazine, trimethyl pyrazine, 2-acetyl pyrazine, 4-methyl-5-(β-hydroxyethyl) thiazole, 2-acetyl thiazole, 2,3,5,6-tetramethyl pyrazine, hexadecanal (strawberry aldehyde and bayberry aldehyde), ethyl vanillin, hydroxyl citronellal, as well as well-known flavoring agents and essences in the art, or a combination thereof.

The amount of flavoring agent in the liquid formulation composition can vary within a relatively large range, as long as the surface tension of the liquid formulation composition is ensured to be within the range described herein. Preferably, the content of the flavoring agent is in the range from about 0.01 wt % to about 5.0 wt %.

To prolong the storage time of the liquid formulation composition and avoid bacteria growth, the liquid formulation composition can further include a bacteriostatic agent, such as, but not limited to, one of parabens or its salts, benzoic acid or its salts, benzyl alcohol, phenylethanol, phenylacetic acid, phenoxyethanol, lauric acid monoglyceride, chlorobutanol, sorbic acid or its salts, calcium propionate, sodium propionate, dehydroacetic acid or its salts, sodium diacetate, glycerol monolaurate, benzalkonium chloride, benzalkonium bromide, cetrimide, chlorhexidine acetate, propanediol, carbon dioxide, nisin, natamycin, momordicin, thimerosal, mercuric nitrate, or a combination thereof.

The amount of bacteriostatic agent in the liquid formulation composition can vary within a relatively large range, as long as the bacteria growth of the liquid formulation composition is ensured to be within the acceptable range. Preferably, the content of the bacteriostatic agent is in the range from about 0.001 wt % to about 2.0 wt %.

The liquid formulation composition of the invention can also include an antioxidant. The antioxidant is selected from, but not limited to, one of tert-butyl hydroxy anisole, butylated hydroxytoluene, tert-butyl hydroquinone, propyl gallate, ascorbyl palmitate, dilauryl thiodipropionate, 4-hexyl resorcinol, tocopherol (vitamin E), L-ascorbic acid, D-sodium erythorbate, tea polyphenols, rosemary extract, ginger extract, sugar alcohols, amino acids or dipeptide type amino acids, or a combination thereof.

The amount of antioxidant in the liquid formulation composition can vary within a relatively large range, as long as the surface tension of the liquid formulation composition is ensured to be within the range described herein. Preferably, the content of the antioxidant is in the range from about 0.001 wt % to about 5.0 wt %.

In the invention, when the liquid formulation composition includes the bacteriostatic agent, the flavoring agent, the stabilizer and the antioxidant, the content of each ingredient in the liquid formulation composition can vary within a relatively large range, for example, as for the liquid formulation composition, the content of the surfactant can be in the range from about 0.1 wt % to about 25.0 wt %, the content of the solvent can be in the range from about 58.0 wt % to about 99.878 wt %, the content of the bacteriostatic agent can be in the range from about 0.001 wt % to about 2.0 wt %, the content of the flavoring agent can be in the range from about 0.01 wt % to about 5.0 wt %, the content of the stabilizer can be in the range from about 0.01 wt % to about 5.0 wt %, and the content of the antioxidant can be in the range from about 0.001 wt % to about 5.0 wt %.

To improve the comprehensive treatment effects of the liquid formulation composition of the invention, preferably, the liquid formulation composition can also include one or more active pharmaceutical ingredients. Active pharmaceutical ingredients include one of medicines for treating rhinitis, sinusitis, lower respiratory tract inflammation, otitis media, otitis externa, xerostomia, xerophthalmia and xeromycteria, or a combination thereof.

Active pharmaceutical ingredients for treating rhinitis, sinusitis and lower respiratory tract inflammation, such as the active pharmaceutical ingredient for treating rhinitis and lower respiratory tract inflammation includes, but not limited to, one of cortisone, hydrocortisone, beclomethasone, triamcinolone acetonide, mometasone, dexamethasone, fluocinolone acetonide, budesonide, fluticasone and other glucocorticoids; ephedrine hydrochloride, xylometazoline hydrochloride and other vasoconstrictors; levocabastine hydrochloride, azelastine hydrochloride and other antihistamines; or fructus xanthii, dandelion, radix scutellariae, bitter gourd, herba ephedrae, flos magnoliae, herba asari, radix angelicae dahuricae, rhizome acori tatarinowii, catechu, Longjing tea, cortex phellodendroni, other traditional Chinese medicines or its extracts, or a combination thereof.

The amount of the active pharmaceutical ingredient employed in the liquid formulation composition of the invention for treating rhinitis, sinusitis and lower respiratory tract inflammation is selected such that it is both effective and safe for administration to a subject.

The liquid formulation composition of the invention can further include one or more active pharmaceutical ingredients for treating otitis externa, otitis media and lower respiratory tract inflammation, for example, the active pharmaceutical ingredient for treating otitis externa, otitis media and lower respiratory tract inflammation includes, but not limited to, one of ofloxacin, levofloxacin, norfloxacin, lomefloxacin, tosufloxacin, sparfloxacin, roxithromycin, chloromycetin, penicillin, clindamycin, nitrofurazone, amoxicillin, ampicillin, clavulanate potassium, cefaclor, cefixime, cefdinir, cephradine, cephalexin, cefpodoxime, cefuroxime axetil, cefprozil, azithromycin, minocycline, acetyl midecamycin, acetylspiramycin or other antibiotics; metronidazole or other antivirals; cortisone, triamcinolone acetonide or other glucocorticoids; and musk, potassium aluminium sulfate anhydrous, calamine, borneol, cochineal, cacumen platycladi, echinacea root, baptisia tinctoria root, other traditional Chinese medicines or its extracts, or a combination thereof.

The amount of the active pharmaceutical ingredient employed in the liquid formulation composition of the invention for treating otitis externa, otitis media and lower respiratory tract inflammation is selected such that it is both effective and safe for administration to a subject.

The liquid formulation composition of the invention can also include one or more ingredients for treating otitis externa, lower respiratory tract inflammation, xeromycteria, xerostomia and xerophthalmia, including but not limited to one of D-panthenol, glycerin, hyaluronic acid, butanediol, polyethylene glycol, propanediol, hexanediol, xylitol, sorbitol, or a combination thereof.

The amount of the active pharmaceutical ingredient employed in the liquid formulation composition of the invention for treating otitis externa, lower respiratory tract inflammation, xeromycteria, xerostomia and xerophthalmia is selected such that it is both effective and safe for administration to a subject.

Exemplarily, in the liquid formulation composition, the content of the active pharmaceutical ingredient can be in the range from about 0.001 wt % to about 5.0 wt %. As described above, in the liquid formulation composition, the content of the surfactant is in the range from about 0.1 wt % to about 25.0 wt %, the content of the solvent is in the range from about 70.0 wt % to about 99.899 wt %, and the content of the active pharmaceutical ingredient is in the range from about 0.001 wt % to about 5.0 wt %. When the liquid formulation composition further contains one of bacteriostatic agent, flavoring agent, stabilizer, antioxidant, or a combination thereof, for the whole liquid formulation composition, the content of the surfactant can be in the range from about 0.1 wt % to about 25.0 wt %, the content of the solvent can be in the range of 53.0 wt % to about 99.877 wt %, the content of the bacteriostatic agent can be in the range from about 0.001 wt % to about 2.0 wt %, the content of the flavoring agent can be in the range from about 0.01 wt % to about 5.0 wt %, the content of the stabilizer can be in the range of 0.01 wt % to about 5.0 wt %, the content of the antioxidant can be in the range from about 0.001 wt % to about 5.0 wt %, and the content of the active pharmaceutical ingredient can be in the range from about 0.001 wt % to about 5.0 wt %.

According to the invention, preferably, the containment vessel is an anti-contaminationسprayer or an anti-contamination dropping device.

In certain embodiments of the invention, the containment vessel for holding the liquid formulation composition is an anti-contamination drug delivery device, such as an anti-contamination sprayer or an anti-contamination dropping device. There are anti-contamination drug delivery devices known in the prior art, such as the Ophthalmic Squeeze Dispenser (OSD) of Aptar Company. The anti-contamination medicine delivery device is based on a pure mechanical principle; and through a drip nozzle sealing technology and an air filtration technology, microbes can be effectively prevented from polluting the liquid formulation composition, and the balance of pressure inside and outside the whole package can be kept. Addition of the bacteriostatic agent is not required, so that the irritation problem caused by the bacteriostatic agent can be greatly reduced; and meanwhile, when the device is adopted, filling can be still performed by using the existing method.

As the anti-contamination medicine delivery device is used for holding the liquid formulation composition, the long-term sterility of the liquid formulation composition can be ensured under the situation where a bacteriostatic agent is not added.

In certain embodiments, if the anti-contamination sprayer or the anti-contamination dropping device is used and when the liquid formulation composition includes the flavoring agent, the stabilizer and the antioxidant, the content of each ingredient in the liquid formulation composition can vary within a relatively large range, for example, as for the whole liquid formulation composition, the content of the surfactant can be in the range from about 0.1 wt % to about 25.0 wt %, the content of the solvent can be in the range of 60.0 wt % to about 99.879 wt %, the content of the flavoring agent can be in the range from about 0.01 wt % to about 5.0 wt %, the content of the stabilizer can be in the range from about 0.01 wt % to about 5.0 wt %, and the content of the antioxidant can be in the range from about 0.001 wt % to about 5.0 wt %.

Under the above situation, if the liquid formulation composition further includes the above-mentioned active pharmaceutical ingredient, at this time, in the liquid formulation composition in the anti-contamination sprayer or the anti-contamination dropping device, the content of the surfactant is in the range of about 0.1 wt % to about 25.0 wt %, the content of the solvent is in the range from about 55.0 wt % to about 99.878 wt %, the content of the flavoring agent is in the range from about 0.01 wt % about 5.0 wt %, the content of the stabilizer is in the range from about 0.01 wt % to about 5.0 wt %, the content of the antioxidant is in the range from about 0.001 wt % to about 5.0 wt %, and the content of the active pharmaceutical ingredient is in the range from about 0.001 wt % to about 5.0 wt %.

According to certain embodiments of the invention, the containment vessel for containing the liquid formulation composition can adopt the various common sprayers or dropping devices in the field of pharmaceuticals. There are no special requirements on the structures of the sprayer and the dropping device in the invention, and the sprayer and the dropping device are commercially available.

Meanwhile, in certain embodiments, the invention provides a preparation method of the formulation. The method includes:

(S1). Dispersing a liquid surfactant in ultrasound of 40 KHz to about 60 KHz for about 1 minute to about 3 minutes;

(S2). Uniformly mixing the liquid surfactant with a solvent under the stirring condition at the rotational speed of more than 3000 rpm to form a liquid formulation composition with liquid particles which contain the surfactant and are dispersed in the solvent, wherein the surface tension of the liquid formulation composition is less than 60 mN/m, and the absolute value of zeta potential is more than 15 mV; and (S3). Filling the liquid formulation composition into a containment vessel, wherein the containment vessel is a sprayer or a dropping device or an anti-contamination sprayer or an anti-contamination dropping device.

In the above preparation method, the surfactant can be selected from one of lecithin, sterol, pulmonary surfactant, poloxamer, dipalmitoyl phosphatidylcholine, cholesterol, cholesteryl ester, phosphatidyl ethanolamine, phosphatidylglycerol, phosphatidylserine, polyethylene glycol, or a combination thereof. Various surfactants meeting the requirements as provided herein can be directly obtained commercially.

The solvent is one of water, ethanol, glycerol, medical silicone oil, edible vegetable oil, or a combination thereof. Preferably, water is chosen as solvent and can reduce the irritation to the user.

According to the invention, in step (S1), when the adopted surfactant raw material is liquid at room temperature, the surfactant can be directly dispersed in ultrasound of 40 KHz to about 60 KHz for about 1 minute to about 3 minutes At this time, the surface tension and the zeta potential of the liquid formulation composition can fall within the range described above by only adjusting the relative content of the solvent and the surfactant. Preferably, in the liquid formulation composition, the content of the surfactant is in the range from about 0.1 wt % to about 25.0 wt %, and the content of the solvent is in the range from about 75.0 wt % to about 99.9 wt %.

When the adopted surfactant is solid at room temperature, the solid surfactant raw material needs to be first processed into the liquid state. Then, the liquid surfactant is dispersed in ultrasound of 40 KHz to about 60 KHz for about 1 minute to about 3 minutes The method for processing the solid surfactant raw material into the liquid state can adopt the method known to the skilled in the art, for example, the solid surfactant raw material can be mixed with a substance which can dissolve the solid surfactant raw material to dissolve. It can be understood that for the different solid active substances, the substances that can dissolve the solid surfactant raw materials may be different. In the invention, the substances that dissolve the solid surfactant raw materials can be any substances known to those of skill in the art, as long as the solid surfactant raw material can be dissolved.

According to the invention, in step (S2), preferably, the surfactant and the solvent are uniformly mixed under the stirring condition at the rotational speed of more than 3000 rpm. At this time, the liquid particles including the surfactant, which have the volume average particle size of less than about 100 μm, can be formed in the solvent. For example, the liquid particles with the volume average particle size in the range from about 1 μm to about 100 μm can be formed. The liquid particles can stably exist in the solvent, and the liquid formulation composition exists as an emulsion. As the liquid particles with the volume average particle size in the range from about 1 μm to about 100 μm are formed in the solvent, the required rotational speed is different for the different liquid surfactants and can be adjusted by those of skill in the art according to actual situations with the benefit of the instant disclosure. As known to those skilled in the art, along with the improvement of the stirring rotational speed and the prolongation of the time, the liquid particles with the smaller volume average particle size can be formed.

Specifically, the solvent and the surfactant are mixed, for example, the surfactant is added into the solvent. After mixing, the surface tension and the zeta potential of the solvent/surfactant mixture are detected, when the surface tension is less than 60 mN/m (or a preset target surface tension value) and the absolute value of zeta potential is more than 15 mV, the formulation is obtained, and the liquid formulation composition disclosed herein can be obtained. The surface tension of the liquid formulation composition can be obtained by testing with an automatic surface tension tester (US Kino, A601). The zeta potential of the liquid formulation composition can be obtained by testing with a zeta potential tester NANOTRAC WAVE (MicroTrac, US). In the preparation method, the specific surfactant and the solvent were adopted and the relative content thereof are as described above, for example, in the liquid formulation composition, the content of the surfactant is in the range from about 0.1 wt % to about 25.0 wt %, and the content of the solvent is in the range from about 75.0 wt % to about 99.9 wt %.

Preferably, after step (S2), the preparation method further includes the steps of ultrasonic crushing or high-pressure homogenization. Through ultrasonic crushing or high-pressure homogenization, the liquid particles can be further homogenized to get smaller liquid particles and form the liquid particles with the volume average particle size in the range from about 50 nm to about 500 nm. Wherein, the liquid particles can be dispersed in the solvent more stably. The volume average particle size of the liquid particles can be directly tested with various existing particle size detection devices (such as laser particle size analyzer Mastersizer 2000 (Malvern Instruments Ltd., UK)).

It can be understood that the liquid particles in the liquid formulation composition can be formed by the surfactant, or by the surfactant and other substances in the liquid formulation composition. The volume average particle size tested with the detection device is the volume average particle size of the liquid particles, including the liquid particles formed by the surfactant or by the surfactant and other substances in the liquid formulation composition.

In certain embodiments of the invention, the stability of the liquid formulation composition can be further improved by adjusting the pH of the liquid formulation composition to the range from about 6.0 to about 7.4. It can be understood that, when the liquid formulation composition is prepared, the pH of initial mixtures including all raw material ingredients, which are obtained by adopting different raw materials, can be different; and if the pH of the initial mixture is within the above range, the pH does not need to be adjusted any more. If the pH is not within the above range, preferably, the pH of the liquid formulation composition can be adjusted through the existing method. For example, the adjustment can be performed through the way of adding a buffer solution. A buffer solution can be selected from a citric acid-sodium citrate buffer solution, an acetic acid-sodium acetate buffer solution, a phosphoric acid buffer solution, an HEPES or Tris-citric acid buffer solution. Preferably, the buffer system is the HEPES and Tris-citric acid buffer solution with the pH in the range from about 6.0 to about 7.4.

The amount of each buffer solution added is selected to allow the pH of the liquid formulation composition to reach the desired level.

According to certain embodiments of the invention, when the liquid formulation composition is prepared, one or more of bacteriostatic agent, flavoring agent, stabilizer, antioxidant can be added according to actual using demands. Examples of bacteriostatic agent, the flavoring agent, the stabilizer and the antioxidant are as described herein.

The amount of each of bacteriostatic agent, flavoring agent, stabilizer and antioxidant is selected as described herein, for example, the adding amount of the surfactant is in the range from about 0.1 wt % to about 25.0 wt %, the adding amount of the solvent is in the range of 58.0-99.878 wt %, the adding amount of the bacteriostatic agent is in the range from about 0.001 wt % to about 2.0 wt %, the adding amount of the flavoring agent is in the range from about 0.01 wt % to about 5.0 wt %, the adding amount of the stabilizer is in the range from about 0.01 wt % to about 5.0 wt %, and the adding amount of the antioxidant is in the range from about 0.001 wt % to about 5.0 wt %.

If the anti-contamination sprayer or the anti-contamination dropping device is used for the preparation of liquid formulation composition, only one of flavoring agent, stabilizer, antioxidant, or a combination thereof can be added, and the bacteriostatic agent does not need to be added. Specifically, the adding amount of each of flavoring agent, stabilizer and antioxidant is also as described herein, for example, the adding amount of the surfactant is in the range from about 0.1 wt % to about 25.0 wt %, the adding amount of the solvent is in the range from about 60.0 wt % to about 99.879 wt %, the adding amount of the flavoring agent is in the range from about 0.01 wt % to about 5.0 wt %, the adding amount of the stabilizer is in the range from about 0.01 wt % to about 5.0 wt %, and the adding amount of the antioxidant is in the range from about 0.001 wt % to about 5.0 wt %.

According to certain embodiments of the invention, when the liquid formulation composition is prepared, one or more active pharmaceutical ingredients can also be added. The active pharmaceutical ingredients include, but not limits to, one of active pharmaceutical ingredient for treating rhinitis, sinusitis, lower respiratory tract inflammation, otitis media, otitis externa, xerostomia, xerophthalmia, xeromycteria, or a combination thereof to enable the liquid formulation composition to have better comprehensive treatment effects. Exemplary active pharmaceutical ingredients are as described herein.

Specifically, there are no particular limitations regarding the step of adding the active pharmaceutical ingredient, for example, the active pharmaceutical ingredient can be mixed with the surfactant and the like together for preparation.

The amount of active pharmaceutical ingredient used is selected so that the liquid formulation composition effective and safe. In specific preparation, the amount of active pharmaceutical ingredient can be adjusted according particular situations by those skilled in the art. Examples amounts of active pharmaceutical ingredient are described herein.

The various active pharmaceutical ingredients added for improving the comprehensive performances of the liquid formulation composition can exist in various forms, including the form of liquid particles. As the adding amount of the various substances are trace amount compared to those of the surfactant and the solvent, the added various substances have little influence on the volume average particle size of the liquid particles in the liquid formulation composition and can be neglected in the invention.

In manufacturing, for example, after the liquid formulation composition is prepared, it is filled into a nasal sprayer or a dropping device (those skilled in the art can select whether to adopt an anti-contamination sprayer or an anti-contamination dropping device as need), and then the nasal sprayer or the dropping device is sealed. After testing for appearance, volume, content of main ingredient, weight per spray (or weight per drop), sedimentation rate, microbial limit and other quality parameters, outside packaging is performed to obtain the final product.

The existing common packages, including containment vessels, pumps (or valves) and triggers, can be adopted for packaging.

The liquid formulation composition of the invention can be filled into the sprayer so as to be used in a form of spray.

The liquid formulation composition of the invention can also be used as nasal drops or ear drops. For the nasal drops or ear drops, the common packages include containment vessels and droppers.

The filling method of the liquid formulation composition is well known by those skilled in the art.

According to the invention, when the anti-contamination sprayer or the anti-contamination dropping device is adopted as the containment vessel, the preparation process of the liquid formulation composition is not affected. When the liquid formulation composition is filled into the anti-contamination sprayer or the anti-contamination dropping device, the filling method is also well known by those skilled in the art.

It is understood that, in the invention, the bacteriostatic agent does not need to be added in the liquid formulation composition when the anti-contamination sprayer or the anti-contamination dropping device is adopted. The content and effects of other components in the liquid formulation composition are not affected by the anti-contamination sprayer or the anti-contamination dropping device.

An objective of the invention is to provide a liquid formulation composition that is stable and can be used in a form of spray or drop, and a preparation method thereof. The formulation can be used in treatment of otitis media, otitis externa, rhinitis, sinusitis, xeromycteria, xerostomia and xerophthalmia.

Without wishing to be bound by the theory, it is believed that the action mechanism of the liquid formulation composition disclosed herein is that the relatively low surface tension is provided at the location to relieve the symptoms. In the description of the invention, only the method of use to otitis media is taken as an example for description. With the benefit of the instant disclosure, those skilled in the art can recognize that the liquid formulation composition provided herein is also effective for other disease symptoms (such as otitis externa, rhinitis, sinusitis and the like) caused by excessive secretion of mucus and blocking of a cavity canal, besides otitis media.

The invention is further described through the following non-limiting examples.

EXAMPLES

Example I

The exemplary embodiment describes a formulation and a preparation method thereof disclosed herein.

2.38 g of hydrogenated phospholipid, 0.12 g of sterol, 0.4 g of methyl paraben, 0.2 g of ethyl paraben and 0.1 g of menthol were weighed and placed in a beaker. 1 mL of anhydrous ethanol was added and dissolved with ultrasonic (40 KHz). While mixing at a high-speed stirring (6000 rpm), water was continuously added till the final volume of 100 mL, and mixed well. The formulation was filled into a containment vessel, such as sprayer or a dropping device, and the containment vessel was sealed. After the results of appearance, volume, content of main ingredient, weight per spray (or weight per drop), microbial limit and other tests were found to meet the requirements, outside packaging was performed to obtain the final product.

The surface tension of a final product was tested to be 48.851 mN/m by an automatic surface tensionmeter (US Kino, A601). The particle size distribution of the product was determined by Mastersizer 2000 (Malvern Instruments Ltd., UK), and the volume average particle size was 2.342 μm. The zeta potential of the product was determined by NANOTRAC WAVE (MicroTrac, US), and the result was −28.5 mV. The pH of the product was determined by a pH meter (Shanghai Leici, PHSJ3F), and the result was 6.2.

After the formulation was centrifuged at 3750 rpm for 5 hours, there was no observable precipitate at the bottom.

Example II

The exemplary embodiment describes a formulation and a preparation method thereof disclosed herein.

2.35 g of soya lecithin, 0.15 g of poloxamer, 0.08 g of vitamin E and 0.5 g of phenylethanol were weighed and placed in a beaker. 1 mL of anhydrous ethanol was added and dissolved with ultrasonic (40 KHz). While mixing at high speed (6000 rpm), water was continuously added till the final volume of 100 mL, and mixed well. The formulation was filled into a containment vessel, such as sprayer or a dropping device and the containment vessel was sealing. After the results of appearance, volume, content of main ingredient, weight per spray (or weight per drop), microbial limit and other tests were found to meet the requirements, outside packaging was performed for preparation to obtain the final product.

The surface tension of a final product was tested to be 16.252 mN/m by an automatic surface tensionmeter (US Kino, A601). The particle size distribution of the product was determined by Mastersizer 2000 (Malvern Instruments Ltd., UK), and the volume average particle size was 5.712 µm. The zeta potential of the product was determined by NANOTRAC WAVE (MicroTrac, US), and the result was −25.8 mV. The pH of the product was determined by a pH meter (Shanghai Leici, PHSJ3F), and the result was 6.1.

After the mixed solution was centrifuged at 3750 rpm for 5 hours, there was no observable precipitate at the bottom.

Example III

The exemplary embodiment describes a formulation and a preparation method thereof disclosed herein.

3.75 g of soya lecithin and 0.64 g of vitamin E were weighed and placed in a beaker. 1 mL of anhydrous ethanol was added and dissolved with ultrasonic (40 KHz). The ethanol solution was added into 0.05 g of lauric acid monoglyceride and 99 mL of Tris-citric acid buffer solution with the pH in the range of 6.0-7.4 while a high-speed stirring (6000 rpm). The ultrasonic homogenization was further performed in an ultrasonic homogenizer. Then, the formulation was filled into containment vessel, such as an anti-contamination medicine delivery device (OSD) and sealed. After the results of appearance, volume, content of main ingredient, weight per spray (or weight per drop), microbial limit and other tests were found to meet the requirements, outside packaging was performed to obtain the final product.

The surface tension of a final product was tested to be 26.225 mN/m by an automatic surface tensionmeter (US Kino, A601). The particle size distribution was determined by Mastersizer 2000 (Malvern Instruments Ltd., UK), and the volume average particle size was 223 nm. The zeta potential of the product was determined by NANOTRAC WAVE (MicroTrac, US), and the result was −32.2 mV. The pH of the product was determined by a pH meter (Shanghai Leici, PHSJ3F), and the result was 6.5.

After centrifugation at 3750 rpm for 5 hours, there was no observable precipitate at the bottom.

Example IV

The exemplary embodiment describes a formulation and a preparation method thereof disclosed herein.

3.75 g of soya lecithin, 0.013 g of vitamin E and 0.1 g of menthol were weighed and placed in a beaker. 1 mL of anhydrous ethanol was added and dissolved with ultrasonic (40 KHz). The ethanol solution was added into 99 mL of water while a high-speed stirring (6000 rpm) and mixed well. Homogenization was performed by a high-pressure homogenizer for 10 minutes. Then, the formulation was filling into containment vessel, such as an anti-contamination medicine delivery device (OSD) and the containment vessel was sealed. After the results of appearance, volume, content of main ingredient, weight per spray (or weight per drop), microbial limit and other tests were found to meet the requirements, outside packaging was performed to obtain the final product.

The surface tension of a final product was tested to be 28.253 mN/m by an automatic surface tensionmeter (US Kino, A601). The particle size distribution was determined by Mastersizer 2000 (Malvern Instruments Ltd., UK), and the volume average particle size was 252 nm. The zeta potential of the product was determined by NANOTRAC WAVE (MicroTrac, US), and the result was −21.2 mV. The pH value of the product was determined by a pH meter (Shanghai Leici, PHSJ3F), and the result was 6.0.

After centrifugation at 3750 rpm for 5 hours, there was no observable precipitate at the bottom.

Example V

The exemplary embodiment describes a formulation and a preparation method thereof disclosed herein.

2.5 g of soya lecithin, 0.01 g of vitamin E, 0.4 g of methyl paraben, 0.2 g of ethyl paraben, 0.5 g of phenylethanol and 0.1 g of menthol were weighed and placed in a beaker. 1 mL of anhydrous ethanol was added and dissolved with ultrasonic (40 KHz). While mixing at high-speed (6000 rpm), 0.12 g of poloxamer was dissolved in 5 mL of water, the water solution containing the poloxamer was mixed with the ethanol solution under high-speed stirring. Water was continuously added till the final volume of 100 mL, and then mixed well. The formulation was filled into a containment vessel, such as sprayer or a dropping device and the containment vessel was sealed. After the results of appearance, volume, content of main ingredient, weight per spray (or weight per drop), microbial limit and other tests were found to meet the requirements, outside packaging was performed to obtain the final product.

The surface tension of a final product was tested to be 20.185 mN/m by an automatic surface tensionmeter (US Kino, A601). The particle size distribution of the product was determined by Mastersizer 2000 (Malvern Instruments Ltd., UK), and the volume average particle size was 4.422 µm. The zeta potential of the product was determined by NANOTRAC WAVE (MicroTrac, US), and the result was −19.8 mV. The pH of the product was determined by a pH meter (Shanghai Leici, PHSJ3F), and the result was 6.1.

After the mixed solution is centrifuged at 3750 rpm for 5 hours, there was no observable precipitate at the bottom.

Example VI

The exemplary embodiment describes a formulation and a preparation method thereof disclosed herein.

3.75 g of soya lecithin, 0.64 g of vitamin E and 0.5 g of phenylethanol were weighed and placed in a beaker. 1 mL of anhydrous ethanol was added and dissolved with ultrasonic (40 KHz). The ethanol solution was added into 99 mL of water containing 0.15 g of poloxamer while a high-speed stirring (6000 rpm), and ultrasonic homogenization was further performed in an ultrasonic homogenizer. Then, the formulation was filled into containment vessel, such as a sprayer or a dropping device and the containment vessel was sealed. After the results of appearance, volume, content of main ingredient, weight per spray (or weight per drop), microbial limit and other tests were found to meet the requirements, outside packaging was performed to obtain the final product.

The surface tension of a final product was tested to be 16.425 mN/m by an automatic surface tensionmeter (US Kino, A601). The particle size distribution was determined by Mastersizer 2000 (Malvern Instruments Ltd., UK), and the volume average particle size was 275 nm. The zeta potential of the product was determined by NANOTRAC WAVE (MicroTrac, US), and the result was −17.8 mV. The pH of the product was determined by a pH meter (Shanghai Leici, PHSJ3F), and the result was 5.9.

After the mixed solution was centrifuged at 3750 rpm for 5 hours, there was no observable precipitate at the bottom.

Example VII

The exemplary embodiment describes a formulation and a preparation method thereof disclosed herein.

1.38 g of hydrogenated phospholipid, 1.0 g of soya lecithin, 0.12 g of sterol, 0.4 g of methyl paraben, 0.2 g of ethyl paraben and 0.1 g of menthol were weighed and placed in a beaker. 1 mL of anhydrous ethanol was added and dissolved with ultrasonic (40 KHz). While mixing at high-speed (6000 rpm), water was continuously added till the final volume of 100 mL and mixed well. The formulation was homogenized for 10 minutes by a high-pressure homogenizer and filled into containment vessel, such as a sprayer or a dropping device, the containment vessel was sealed. After the results of appearance, volume, content of main ingredient, weight per spray (or weight per drop), microbial limit and other tests were found to meet the requirements, outside packaging was performed to obtain the final product.

The surface tension of a final product was tested to be 28.518 mN/m by an automatic surface tensionmeter (US Kino, A601). The particle size distribution of the product was determined by Mastersizer 2000 (Malvern Instruments Ltd., UK), and the volume average particle size was 356 nm. The zeta potential of the product was determined by NANO-TRAC WAVE (MicroTrac, US), and the result was −35.8 mV. The pH of the product was determined by a pH meter (Shanghai Leici, PHSJ3F), and the result was 6.2.

After the mixed solution was centrifuged at 3750 rpm for 5 hours, there was no observable precipitate at the bottom.

Example VIII

The exemplary embodiment describes a formulation (containing a active pharmaceutical ingredient for treating rhinitis and sinusitis) and a preparation method thereof disclosed herein.

1.0 g of soya lecithin, 0.12 g of sterol, 4 mg of triamcinolone acetonide, 0.4 g of methyl paraben, 0.2 g of ethyl paraben and 0.1 g of menthol were weighed and placed in a beaker. 1 mL of anhydrous ethanol was added and dissolved with ultrasonic (40 KHz). While mixing at high-speed stirring (6000 rpm), water was continuously added till the final volume of 100 mL and mixed well. The formulation was homogenized for 10 minutes by a high-pressure homogenizer and filled into containment vessel, such as a sprayer or a dropping device. The containment vessel was sealed. After the results of appearance, volume, content of main ingredient, weight per spray (or weight per drop), microbial limit and other tests were found to meet the requirements, outside packaging was performed for preparation to obtain the final product.

The surface tension of a final product was tested to be 24.518 mN/m by an automatic surface tensionmeter (US Kino, A601). The particle size distribution of the product was determined by Mastersizer 2000 (Malvern Instruments Ltd., UK), and the volume average particle size was 305 nm. The zeta potential of the product was determined by NANO-TRAC WAVE (MicroTrac, US), and the result was −25.8 mV. The pH of the product was determined by a pH meter (Shanghai Leici, PHSJ3F), and the result was 5.7.

After the mixed solution was centrifuged at 3750 rpm for 5 hours, there was no observable precipitate at the bottom.

Example IX

The exemplary embodiment describes a formulation (containing a active pharmaceutical ingredient for treating otitis media) and a preparation method thereof disclosed herein.

1.0 g of soya lecithin, 0.12 g of sterol, 0.4 g of methyl paraben, 0.2 g of ethyl paraben and 0.1 g of menthol were weighed and placed in a beaker. 1 mL of anhydrous ethanol was added and dissolved with ultrasonic (40 KHz). While mixing at high-speed (6000 rpm), a water solution containing 0.3 wt % of levofloxacin hydrochloride (calculated by levofloxacin) was continuously added till the final volume of 100 mL and mixed well. The formulation was homogenized for 10 minutes by a high-pressure homogenizer, and filled into containment vessel, such as a sprayer or a dropping device. The containment vessel was sealed. After the results of appearance characters, volume, content of main ingredient, weight per spray (or weight per drop), microbial limit and other tests were found to meet the requirements, outside packaging was performed to obtain the final product.

The surface tension of a final product was tested to be 27.184 mN/m by an automatic surface tensionmeter (US Kino, A601). The particle size distribution of the product was determined by Mastersizer 2000 (Malvern Instruments Ltd., UK), and the volume average particle size was 235 nm. The zeta potential of the product was determined by NANO-TRAC WAVE (MicroTrac, US), and the result was −43.9 mV. The pH value of the product was determined by pH meter (Shanghai Leici, PHSJ3F), and the result was 5.8.

After the mixed solution was centrifuged at 3750 rpm for 5 hours, there was no observable precipitate at the bottom.

Example X

The exemplary embodiment is used for describing a formulation and a preparation method thereof disclosed herein.

0.1 g of Poloxamer 188, 0.8 mg of phenylethanol were weighed and placed in a beaker. Water was added to make up 100 mL to dissolve and mix well. The solution was filled into containment vessel, such as a sprayer or a dropping device. The containment vessel was sealed. After the results of appearance characters, volume, content of main ingredient, weight per spray (or weight per drop), microbial limit and other tests were found to meet the requirements, outside packaging was performed to obtain the final product.

The surface tension of a final product was tested to be 25.851 mN/m by an automatic surface tensionmeter (US Kino, A601). The pH value of the product was determined by pH meter (Shanghai Leici, PHSJ3F), and the result was 5.7.

Example XI

The exemplary embodiment is used for describing a formulation (containing a active pharmaceutical ingredient for treating rhinitis and sinusitis) and a preparation method thereof disclosed herein.

0.1 g of Poloxamer 188, 0.8 mg of phenylethanol, and 60 mg of dexamethasone sodium phosphate (calculated as dexamethasone) were weighed and placed in a beaker. 10 mL of water was added to dissolve completely. Tris-citric acid buffer at pH 6.5 was added in to the obtained mixture solution till final volume to 100 mL, mixed well and filled into containment vessel, such as a sprayer or a dropping device. The containment vessel was sealed. After the results of appearance characters, volume, content of main ingredient, weight per spray (or weight per drop), microbial limit and other tests were found to meet the requirements, outside packaging was performed to obtain the final product.

The surface tension of a final product was tested to be 25.512 mN/m by an automatic surface tensionmeter (US Kino, A601). The pH value of the product was determined by pH meter (Shanghai Leici, PHSJ3F), and the result was 6.5.

Example XII

The exemplary embodiment describes a formulation (containing a active pharmaceutical ingredient for treating otitis media) and a preparation method thereof disclosed herein.

0.1 g of Poloxamer 188, 0.3 g of levofloxacin hydrochloride (calculated as levofloxacin) were weighed and placed in a beaker. 10 mL of water was added to dissolve completely. HEPES buffer at pH 6.0 was added in to the obtained mixture solution till final volume to 100 mL and mixed well and filled into containment vessel, such as a sprayer or a dropping device. The containment vessel was sealed. After the results of appearance characters, volume, content of main ingredient, weight per spray (or weight per drop), microbial limit and other tests were found to meet the requirements, outside packaging was performed to obtain the final product.

The surface tension of a final product was tested to be 24.125 mN/m by an automatic surface tensionmeter (US Kino, A601). The pH value of the product was determined by pH meter (Shanghai Leici, PHSJ3F), and the result was 6.0.

Comparative Example I

The exemplary comparative example is used for comparative description of a liquid formulation composition and a preparation method thereof disclosed herein.

2.5 g of hydrogenated phospholipid was weighed and placed in a containment vessel. Water was added till the final volume of 100 mL, and dissolved with ultrasonic (40 KHz), while mixing with a magnetic stirrer for 30 minutes.

The particle size distribution of the product was determined by Mastersizer 2000 (Malvern Instruments Ltd., UK), and the volume average particle size was 525.234 μm. The zeta potential of the product was determined by NANOTRAC WAVE (MicroTrac, US), and the result was −2.5 mV. The pH of the product was determined by a pH meter (Shanghai Leici, PHSJ3F), and the result was 5.7.

After the mixed solution was centrifuged at 3750 rpm for 5 hours, there was significant amount of precipitate at the bottom.

Comparative Example II

The exemplary comparative example is used for comparative description of a liquid formulation composition and a preparation method thereof disclosed herein.

5.0 g of soybean phospholipid, 1.0 g of vitamin E and 0.5 g of phenylethanol were weighed and placed in a containment vessel, 100 mL of water was added in a manual stirring state, and mixed.

The particle size distribution was determined by Mastersizer 2000 (Malvern Instruments Ltd., UK), and the volume average particle size was 785.347 The zeta potential of the product was determined by NANOTRAC WAVE (MicroTrac, US), and the result was −2.2 mV. The pH of the product was determined by a pH meter (Shanghai Leici, PHSJ3F), and the result was 5.7.

After the mixed solution was centrifuged at 3750 rpm for 5 hours, there was significant amount of precipitate at the bottom.

Performance Testing

The exemplary performance testing is performed on the liquid formulation composition prepared by the preparation method as follows:

1. Efficacy Test on Animal Model of Otitis Media

The guinea pigs were subjected to general anesthesia by intramuscular injection of 70 mg/kg of ketamine and subcutaneous injection of 30 mg/Kg of pentobarbital. Followed by injecting inactivated *Haemophilus influenzae* in tympanic cavity to establish the secretory otitis media animal model. Experimental animals were variegated guinea pigs, and randomly grouped into a normal animal group with 10 animals and 3 model groups with 30 successfully modeled animals. The model animals were randomly grouped into a non-treatment group, a saline treatment group and a formulation treatment group, 10 animals for each group. The liquid formulation composition prepared in Example II was employed for treatment by nasal spray. For each guinea pig, the amount of each nasal spray is 2.5 mg, the amount for bilateral nasal cavities was 5 mg and the liquid formulation composition was sprayed twice every day for 7 consecutive days. Tympanograms and auditory brainstem response (ABR) thresholds were recorded, and single-factor analysis of variance was adopted for statistical analysis.

TABLE 1

| Tympanic cavity pressures of groups (da Pa) | | | |
|---|---|---|---|
| Group | Number | Mean | SD |
| Normal group | 20 | 33.06 | 18.75 |
| Non-treatment group | 20 | 140.6 | 26.00 |
| Saline group | 20 | 129.0 | 21.94 |
| Formulation group | 20 | 28.21 | 16.78 |

TABLE 2

| LSD Multiple comparisons of tympanic cavity pressures between groups | | | |
|---|---|---|---|
| Group | Comparative group | Mean difference | P value |
| Formulation group | Non-treatment group | 112.4* | 0.000 |
| Formulation group | Saline group | 100.8* | 0.000 |
| Non-treatment group | Normal group | 107.6* | 0.000 |
| Non-treatment group | Saline group | 11.62 | 0.252 |

Note:
*The difference has statistical significance ($P < 0.05$)

TABLE 3

| ABR thresholds (dB) | | | |
|---|---|---|---|
| Group | Number | Mean | SD |
| Normal group | 10 | 14.9 | 3.0 |
| Non-treatment group | 10 | 53.0 | 4.3 |
| Saline group | 10 | 52.6 | 4.9 |
| Formulation group | 10 | 24.6 | 3.6 |

TABLE 4

LSD Multiple comparisons of response thresholds between groups

| Group | Comparative group | Mean difference | P value |
|---|---|---|---|
| Formulation group | Non-treatment group | 28.4* | 0.000 |
| Formulation group | Saline group | 28.0* | 0.000 |
| Formulation group | Normal group | 9.73* | 0.000 |
| Non-treatment group | Saline group | 0.400 | 0.513 |

Note:
*The difference has statistical significance (P < 0.05)

The results showed that the ABR threshold of the normal group was (14.9±3.0) dB HL.

The ABR threshold of the non-treatment group increased to (53.0±4.3) dB HL, and had statistical significance in comparison with that of the normal group.

The ABR threshold of the saline group was (52.6±4.9) dB HL, and had no statistical significance in comparison with that of the non-treatment group.

After treatment with nasal spray formulation for 7 days, the ABR threshold of the formulation group reduced to (24.6±3.6) dB HL, and had statistical significance in comparison with those of the non-treatment group and the saline group.

Therefore, by the treatment using the liquid formulation composition of the invention, the middle ear negative pressures and the ABR thresholds of the guinea pigs with secretory otitis media were significantly reduced, and the improvement of these indicators was transformed to rapid relief of above-mentioned symptoms of otitis media in clinical.

Based on the similar mechanism, the liquid formulation composition of the invention has the same effects for relieving the symptoms of otitis externa, rhinitis and sinusitis.

2. Testing of Sedimentation Stability

Two final products (0.5 mL/vial) were respectively taken from Example II, Example IV and Comparative example II, and centrifuged at 3750 rpm for 5 hours for sedimentation stability test. By visual observation, as shown in FIG. 1, no observable precipitate was found in each of Example II and Example IV, while the obvious precipitates were found in Comparative example II.

In the above test, the result of centrifugation at 3750 rpm for 5 hours equaled to that of normal storage 1 year. As shown in FIG. 1, the liquid formulation composition disclosed herein had desirable stability.

The above exemplary embodiments are only examples and/or preferable embodiments of the invention and are not intended to limit the invention. Any modifications, equivalent substitutions, improvements and the like made within the spirit and the mechanism of the invention should be protected within the scope of the invention.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

What is claimed is:

1. A medicament delivery device, consisting of:
   a containment vessel for holding a liquid comprising an outlet; and
   a liquid formulation composition held in the containment vessel, the liquid formulation composition consisting of water as a solvent, poloxamer, D-panthenol, methyl paraben, a phospholipid, and one or more of a bacteriostatic agent, a flavoring agent, a stabilizer and an antioxidant,
   wherein
   the liquid formulation composition is an emulsion of liquid droplets having volume average particle sizes in the range from about 1 μm to about 100 μm, and is characterized by
   the phospholipid is present in an amount of about 0.0001 wt % to about 25.0 wt %,
   poloxamer is present in an amount of about 0.01 wt % to about 5.0 wt %,
   methyl paraben is present in an amount of about 0.001 wt % to about 2.0 wt %,
   a surface tension of less than 30 mN/m, and
   a pH value from 6.0 to 7.4.

2. The medicament delivery device of claim 1, wherein the containment vessel is configured to function as a sprayer, allowing controlled spraying of the liquid formulation composition out of the outlet.

3. The medicament delivery device of claim 1, wherein the containment vessel is configured to function as a dropping device, allowing controlled dropping of the liquid formulation composition out of the outlet.

4. The medicament delivery device of claim 1, wherein the liquid formulation composition consists of water as a solvent, poloxamer, D-panthenol, methyl paraben and a phospholipid, a bacteriostatic agent, a flavoring agent, a stabilizer, and an antioxidant.

5. The medicament delivery device of claim 1, characterized by an absolute value of zeta potential of greater than 15 mV for the liquid particles.

6. The medicament delivery device of claim 4, wherein the content of the bacteriostatic agent is in the range from 0.001 wt % to 2.0 wt %,
the content of the flavoring agent is in the range from 0.01 wt % to 5.0 wt %, and
the content of the antioxidant is in the range from 0.001 wt % to 5.0 wt %.

* * * * *